(12) United States Patent  
Sano et al.

(10) Patent No.: US 11,276,313 B2  
(45) Date of Patent: Mar. 15, 2022

(54) INFORMATION PROCESSING DEVICE, DRIVE ASSIST SYSTEM, AND DRIVE ASSIST METHOD

(71) Applicant: FUJITSU LIMITED, Kawasaki (JP)

(72) Inventors: Satoshi Sano, Kawasaki (JP); Yasuhiko Nakano, Kawasaki (JP); Koji Oguri, Nagakute (JP); Haruki Kawanaka, Nagakute (JP); Yosuke Fujisawa, Nagakute (JP)

(73) Assignee: FUJITSU LIMITED, Kawasaki (JP)

( * ) Notice: Subject to any disclaimer, the term of this patent is extended or adjusted under 35 U.S.C. 154(b) by 120 days.

(21) Appl. No.: 16/694,453

(22) Filed: Nov. 25, 2019

(65) Prior Publication Data

US 2020/0090518 A1 Mar. 19, 2020

Related U.S. Application Data

(63) Continuation of application No. PCT/JP2017/020364, filed on May 31, 2017.

(51) Int. Cl.
*A61B 5/18* (2006.01)
*G08G 1/16* (2006.01)
(Continued)

(52) U.S. Cl.
CPC ............. *G08G 1/166* (2013.01); *A61B 5/163* (2017.08); *A61B 5/18* (2013.01); *B60R 1/06* (2013.01);
(Continued)

(58) Field of Classification Search
CPC .... G08G 1/166; G08G 1/0125; B60R 21/013; B60R 1/06; A61B 5/18; A61B 5/163
See application file for complete search history.

(56) References Cited

U.S. PATENT DOCUMENTS 6,249,720 B1    6/2001  Kubota et al.
2007/0089054 A1 4/2007  Morimoto
(Continued)

FOREIGN PATENT DOCUMENTS

JP  07-167668   7/1995
JP  11-250395   9/1999
(Continued)

OTHER PUBLICATIONS

EESR—Extended European Search Report dated Jun. 9, 2020 for corresponding European Patent Application No. 17911992.0.
(Continued)

*Primary Examiner* — Mathew Franklin Gordon
(74) *Attorney, Agent, or Firm* — Fujitsu Patent Center

(57) ABSTRACT

An information processing device includes: a memory; and a processor coupled to the memory and configured to: detect an environment around a vehicle which is driven by a driver; generate a hazard list of an object to be a hazard based on the detected environment; detect a gaze of the driver; evaluate a risk regarding driving of the driver for each object included in the hazard list based on a frequency at which the object included in the hazard list is included in a field of view of the driver based on the detected gaze; and output drive assist information corresponding to the object with the evaluated risk that is equal to or larger than a threshold.

20 Claims, 20 Drawing Sheets

(51) Int. Cl.
*G08G 1/0962* (2006.01)
*B60R 1/06* (2006.01)
*B60R 21/00* (2006.01)
*A61B 5/16* (2006.01)
*B60R 21/013* (2006.01)
*G08G 1/01* (2006.01)

(52) U.S. Cl.
CPC ......... *B60R 21/013* (2013.01); *G08G 1/0125* (2013.01)

(56) References Cited

U.S. PATENT DOCUMENTS

| | | | | |
|---|---|---|---|---|
| 2011/0169625 | A1* | 7/2011 | James | G08G 1/166 340/439 |
| 2012/0271484 | A1 | 10/2012 | Feit et al. | |
| 2013/0325478 | A1 | 12/2013 | Matsumoto et al. | |
| 2014/0176813 | A1* | 6/2014 | Conness | G06F 3/165 348/738 |
| 2016/0272215 | A1 | 9/2016 | Laine | |
| 2018/0326982 | A1* | 11/2018 | Paris | G05D 1/0088 |

FOREIGN PATENT DOCUMENTS

| | | |
|---|---|---|
| JP | 2003-099899 | 4/2003 |
| JP | 2005-004414 | 1/2005 |
| JP | 2006-219077 | 8/2006 |
| JP | 2007-094618 | 4/2007 |
| JP | 2008-040974 | 2/2008 |
| JP | 2009-009320 | 1/2009 |
| JP | 2010-182085 | 8/2010 |
| JP | 2012-128654 | 7/2012 |
| JP | 2013-514592 | 4/2013 |
| JP | 2013-242763 | 12/2013 |
| JP | 2017-68641 | 4/2017 |
| JP | 2017-138687 | 8/2017 |

OTHER PUBLICATIONS

JPOA—Japanese Office Action dated Aug. 4, 2020 for corresponding Japanese Patent Application No. 2019-521624 with Machine Translation.

ISR—International Search Report with English translation and Written Opinion and English translation of relevant part [Form PCT/ISA/210, PCT/ISA/220, PCT/ISA/237] for International Application No. PCT/JP2017/020364 dated Sep. 5, 2017.

* cited by examiner

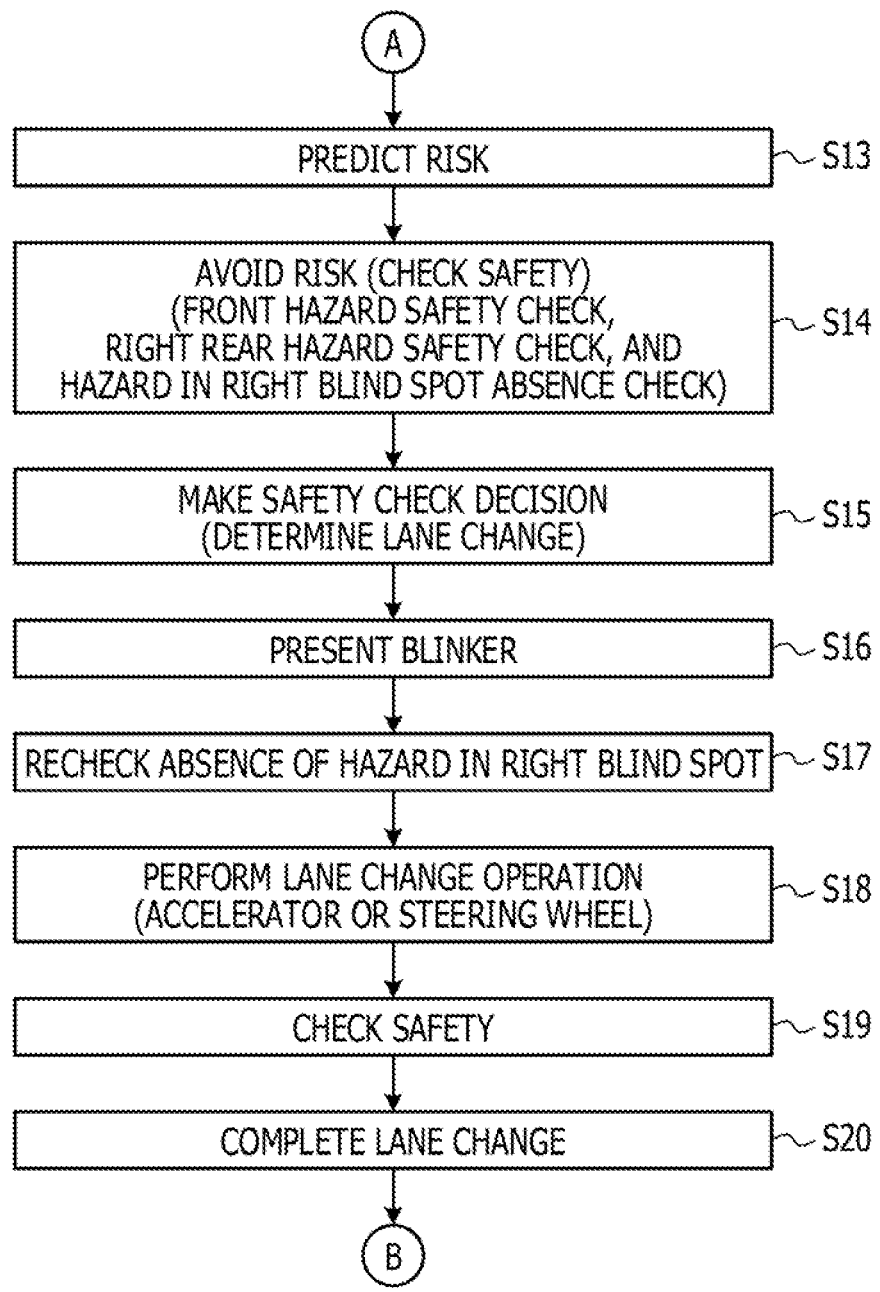

FIG. 4A

ACTION INFORMATION — 127

| POSITION | SITUATION | ID | CALL ATTENTION MESSAGE | DIRECTION TO BE CHECKED | VIRTUAL OUTPUTTING PERSON |
|---|---|---|---|---|---|
| INTERSECTION | STRAIGHT AHEAD | 1 | "CAUTION, INTERSECTION" | FRONT | VIRTUAL OUTPUTTING PERSON OUTSIDE AND IN FRONT OF VEHICLE |
| | | 2 | "CHECK LEFT" | LEFT SIDE | VIRTUAL OCCUPANT IN PASSENGER'S SEAT |
| | | 3 | "CHECK RIGHT" | RIGHT SIDE | VIRTUAL OUTPUTTING PERSON ON RIGHT SIDE OUTSIDE VEHICLE |
| | RIGHT TURN | 4 | "CAUTION, INTERSECTION. STOP AND CHECK" | FRONT | VIRTUAL OUTPUTTING PERSON OUTSIDE AND IN FRONT OF VEHICLE |
| | | 5 | "CHECK RIGHT FRONT" | RIGHT FRONT | VIRTUAL OUTPUTTING PERSON OUTSIDE AND IN RIGHT FRONT OF VEHICLE |
| | | 6 | "CHECK PEDESTRIAN" | AHEAD OF RIGHT TURN | VIRTUAL OCCUPANT ON REAR RIGHT SIDE |
| | LEFT TURN | 7 | "CAUTION, INTERSECTION. STOP AND CHECK" | FRONT | VIRTUAL OUTPUTTING PERSON OUTSIDE AND IN FRONT OF VEHICLE |
| | | 8 | "CAUTION, AHEAD OF LEFT TURN" | AHEAD OF LEFT TURN | VIRTUAL OCCUPANT IN PASSENGER'S SEAT |
| | | 9 | "CAUTION AND CHECK TWO-WHEELED VEHICLE" | LEFT REAR | VIRTUAL OCCUPANT ON REAR LEFT SIDE |
| | ... | ... | ... | ... | ... |

FIG. 4B

| TIMING | ORDER | ACTION INFORMATION ||| |
|---|---|---|---|---|
| | | POINTING DIRECTION | CHECK ACTION ||
| | | | CALL CONTENT | GAZE DIRECTION |
| BEFORE (L/V - 10) SECONDS | 1 | FRONT | "STOP CLEAR" | FRONT |
| BEFORE (L/V - 5) SECONDS | 2 | LEFT SIDE | "LEFT SIDE CLEAR" | LEFT SIDE |
| BEFORE (L/V) SECONDS | 3 | RIGHT SIDE | "RIGHT SIDE CLEAR" | RIGHT SIDE |
| BEFORE (L/V - 10) SECONDS | 1 | FRONT | "STOP CLEAR" | FRONT |
| BEFORE (L/V - 5) SECONDS | 2 | RIGHT FRONT | "RIGHT FRONT CLEAR" | RIGHT FRONT |
| BEFORE (L/V) SECONDS | 3 | AHEAD OF RIGHT TURN | "NO PEDESTRIAN" | AHEAD OF RIGHT TURN |
| BEFORE (L/V - 10) SECONDS | 1 | FRONT | "STOP CLEAR" | FRONT |
| BEFORE (L/V - 5) SECONDS | 2 | AHEAD OF LEFT TURN | "AHEAD OF LEFT TURN CLEAR" | AHEAD OF LEFT TURN |
| BEFORE (L/V) SECONDS | 3 | LEFT REAR | "CHECK TWO-WHEELED VEHICLE" | LEFT REAR |
| ... | ... | ... | ... | ... |

| POSITIONAL RELATIONSHIP | | DISTANCE | | OBJECT | | INTEREST DEGREE (RISK DEGREE) | |
|---|---|---|---|---|---|---|---|
| | | | | | | | FORGETTING COEFFICIENT |
| | | | | | | | × |
| | | | | | | CHECK FREQUENCY | |
| | | | | | | CHECK CENTRAL FIELD OF VIEW | |
| | | | | | | CHECK PERIPHERAL FIELD OF VIEW | |
| | | | | | | CHECK CALL | |
| | | | | | | CHECK REPEATED CALL | |
| | | | | | | DIRECT CHECK | |
| | | | | | | INDIRECT CHECK (RECALL) | |
| | | | | | | ... | |
| | | | | × | | | |
| | | | | RELATIVE SPEED | | | |
| | | | | ONCOMING VEHICLE | | | |
| | | | | PEDESTRIAN | | | |
| | | | | OVERTAKING VEHICLE | | | |
| | | | | LOW-SPEED VEHICLE | | | |
| | | | | LEADING VEHICLE | | | |
| | | | | FOLLOWING VEHICLE | | | |
| | | | | VEHICLE TRAVELING PARALLEL | | | |
| | | | | ... | | | |
| | | × | | | | | |
| | | 300 | | | | | |
| | | 200 | | | | | |
| | | 100 | | | | | |
| | | 80 | | | | | |
| | | 50 | | | | | |
| | | 30 | | | | | |
| | | 10 | | | | | |
| | | ... | | | | | |
| | × | | | | | | |
| CENTER DIVIDER | | | | | | | |
| LEFT SIDE STRIP | | | | | | | |
| DRIVING LANE | | | | | | | |
| RIGHT SIDE STRIP | | | | | | | |
| ONCOMING LANE | | | | | | | |
| LEFT SIDEWALK | | | | | | | |
| RIGHT SIDEWALK | | | | | | | |
| ... | | | | | | | |

ROAD CONSTRUCTION

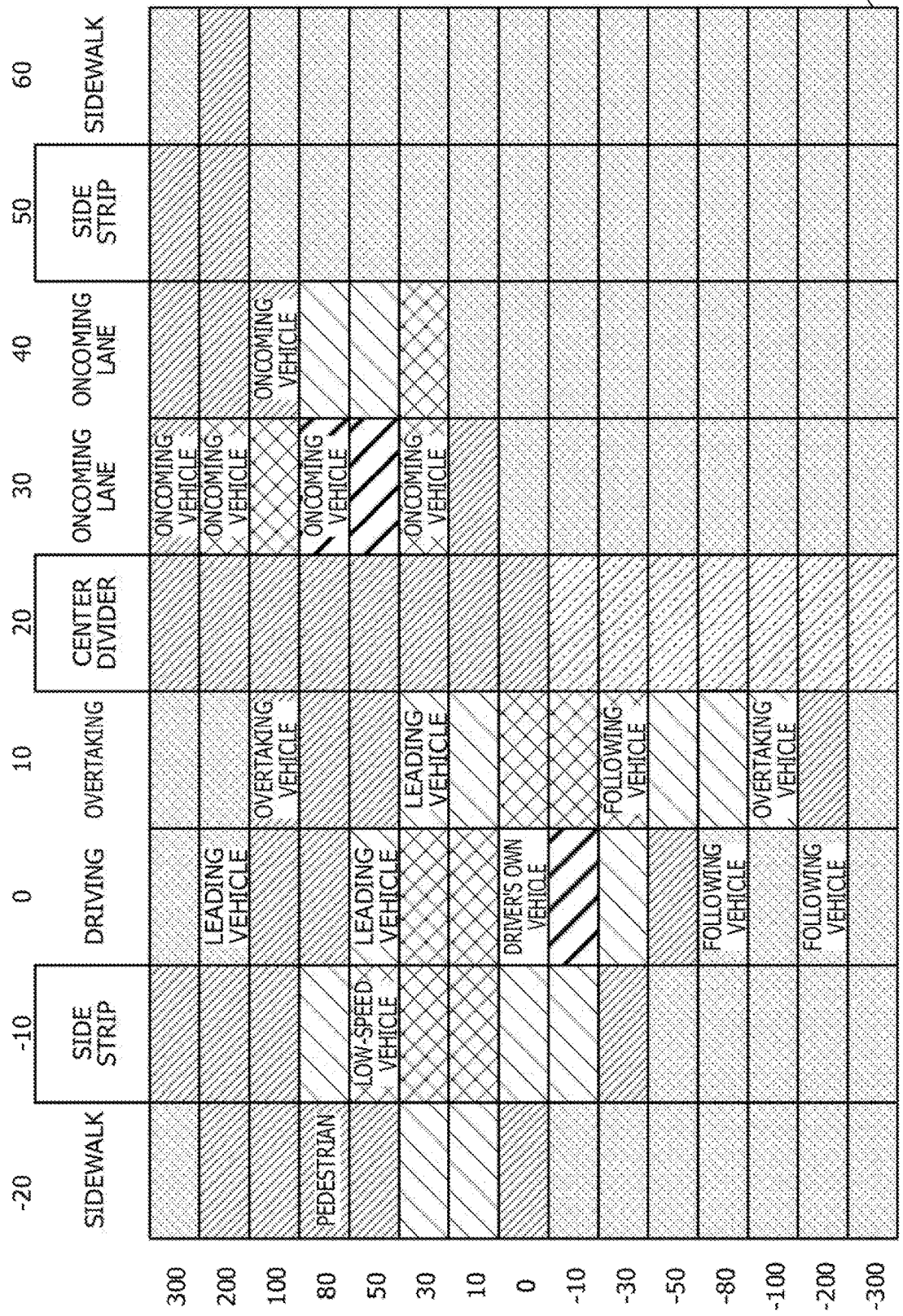

FIG. 13

|  | DRIVER | VIRTUAL OUTPUTTING PERSON |
|---|---|---|
| #1 | "VEHICLE IN FRONT! DECELERATE" | – |
| #2 | "REAR CLEAR!" | – |
| #3 | – | "CAUTION, RIGHT!" |
| #4 | "RIGHT CLEAR! POINTING CALL TO SIDE MIRROR" | – |
| #5 | – | CLEAR SOUND + "RIGHT CLEAR!" |
| #6-7 | DIRECT CHECK, LANE CHANGE | – |
| ⋮ | ⋮ | ⋮ |

INFORMATION PROCESSING DEVICE, DRIVE ASSIST SYSTEM, AND DRIVE ASSIST METHOD

CROSS-REFERENCE TO RELATED APPLICATION

This application is a continuation application of International Application PCT/JP2017/020364 filed on May 31, 2017 and designated the U.S., the entire contents of which are incorporated herein by reference.

FIELD

Embodiments relate to a drive assist device, a drive assist system, and a drive assist method.

BACKGROUND

Drive assist devices that notifies drivers of the presence of hazardous places, obstacles, and the like (hazard objects) in vehicles or the like to call drivers' attention are provided.

Related art is disclosed in Japanese Laid-open Patent Publication No. 2008-40974, Japanese Laid-open Patent Publication No. 2003-99899, Japanese Laid-open Patent Publication No. 7-167668 and Japanese Laid-open Patent Publication No. 2005-4414.

SUMMARY

According to an aspect of the embodiments, an information processing device includes: a memory; and a processor coupled to the memory and configured to: detect an environment around a vehicle which is driven by a driver; generate a hazard list of an object to be a hazard based on the detected environment; detect a gaze of the driver; evaluate a risk regarding driving of the driver for each object included in the hazard list based on a frequency at which the object included in the hazard list is included in a field of view of the driver based on the detected gaze; and output drive assist information corresponding to the object with the evaluated risk that is equal to or larger than a threshold.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 2A and 2B are an explanatory diagram for describing a cognitive structure model of a driver.

FIGS. 4A and 4B are an explanatory diagram for describing an example of an action information storage unit.

FIG. 11 is an explanatory diagram illustrating risk calculation.

FIGS. 12A and 12B are an explanatory diagram for describing examples of a hazard map and a risk map.

FIG. 13 is an explanatory diagram for describing examples of check actions.

DESCRIPTION OF EMBODIMENTS

Figure 1:
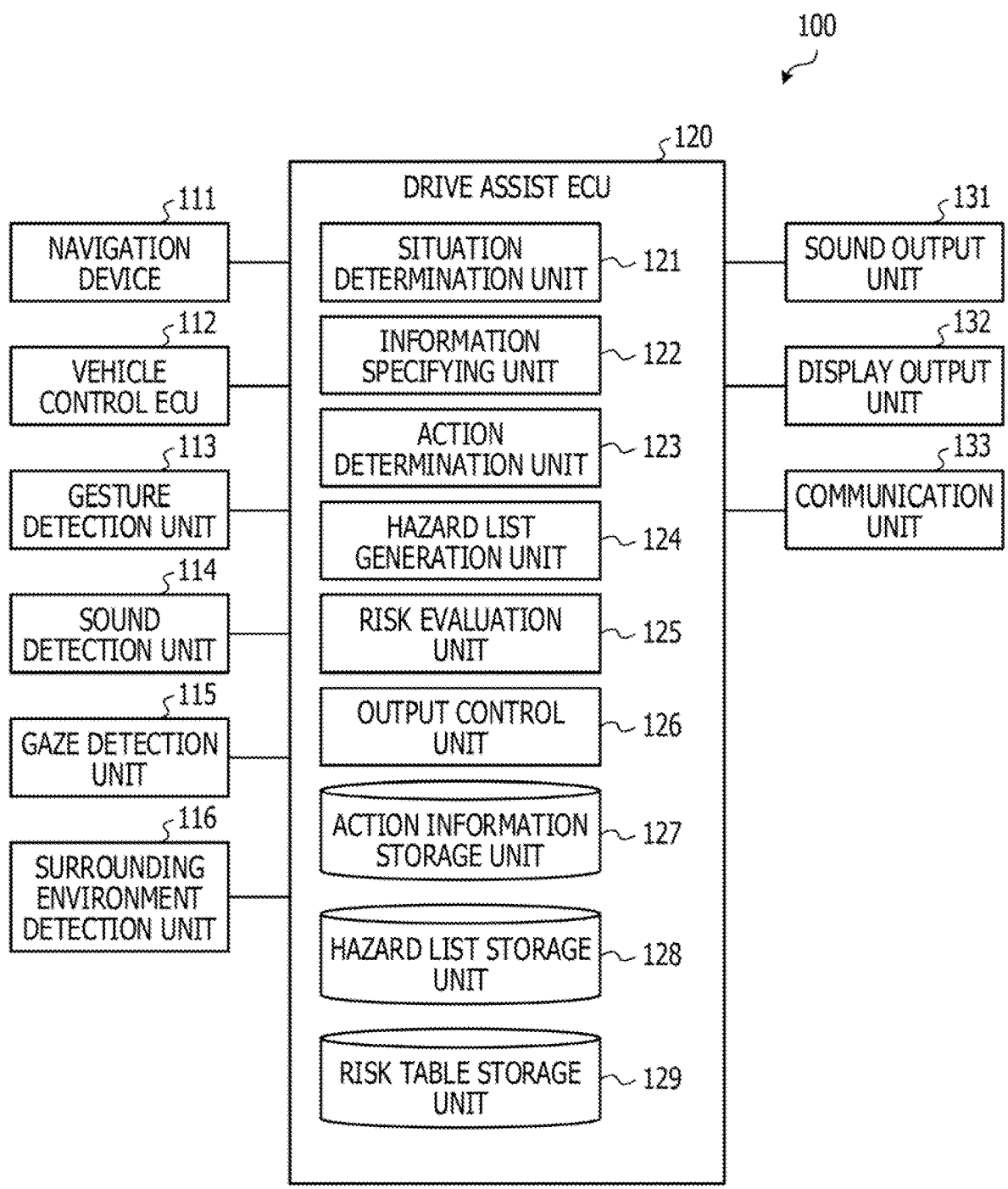
FIG. 1 is a block diagram of a functional configuration of a drive assist device according to a first embodiment.

For example, the drive assist device displays a name, a code, and the like for specifying the hazardous place or the like in a gaze direction of when the driver looks at the hazardous place or the like, and determines whether a sound uttered by the driver matches a sound pattern of the displayed name, code, or the like. Then, in a case where the uttered sound does not match the sound pattern within a predetermined time after the name, code, or the like for specifying the hazardous place or the like is displayed, the drive assist device issues a warning to the driver.

However, warnings are sometimes excessively issued for cognitive activities of the driver, and drive assist is sometimes excessively performed.

For example, in a case where the drive assist is excessively performed, such as issuance of warnings to the driver, although the driver sufficiently recognizes the hazardous place or the like, the driver's tendency to depend on the drive assist becomes stronger. The driver who has strong dependence on the drive assist has less cognitive activities for hazardous places, and for example, the prediction ability for the hazardous places is less improved. Thus, the excessive drive assist may not lead to assist for the driver's cognitive activities.

A drive assist device, a drive assist system, and a drive assist method for realizing appropriate drive assist for the driver may be provided.

Hereinafter, a drive assist device, a drive assist system, and a drive assist method according to embodiments will be described with reference to the drawings. Configurations having the same functions in the embodiments are denoted by the same reference signs, and redundant description will be omitted. Note that the drive assist device, the drive assist system, and the drive assist method to be described in the following embodiment are merely examples and thus do not limit the embodiments. In addition, the embodiments below may be appropriately combined unless otherwise contradicted.

Note that, in the following embodiments, "call attention message" refers to drive assist information for calling driver's attention regarding drive operation in a vehicle or the like.

In addition, a "driver" refers to an object person to which sounds of the call attention message are output to assist driving. In the following embodiments, cases where the object person is located at a position of a driver's seat for driving and operating the vehicle will be described. However, even if the driver is not at the position of the driver's seat, a person who is located at the position where the person can perform the drive operation is also included in the driver.

In addition, a "virtual outputting person" refers to a virtual sound source that outputs various types of sound information including the call attention message by sounds. When outputting the sound information via a plurality of sound output units (sound output devices such as speakers) arranged around the driver who is performing the drive operation, the virtual sound source can be arranged in an arbitrary direction around the driver by controlling a volume (sound pressure) and a phase. For example, the driver may be caused to recognize as if persons having predetermined attributes exist in respective directions in which the virtual sound sources are arranged by changing voice sound for each of the virtual sound sources.

Note that, a virtual sound source arranged at a position corresponding to the position of the seat around the driver, among the virtual outputting persons, is referred to as a "virtual occupant".

In addition, "check action" refers to an action (a motion for grasping a driving environment or situation such as grasping of an external object by visual observation, check of an operation panel or a rearview mirror, for example) performed by the driver for check according to a situation (right or left turn, overtaking, or the like, for example) of the vehicle operated by the driver.

Further, "call" refers to a check action performed by utterance among check actions of the driver. Note that the check actions include a pointing action, a movement of a gaze, and the like, in addition to the call. Furthermore, the "call" includes information provision from the "virtual occupant" by a peripheral monitoring function by a vehicle sensor.

Further, "repeated call" means that virtual occupants output information (repeated call information) corresponding to content of the call by sounds at the same time after the call (note that the output may not be necessarily perfectly at the same time, and there may be a gap to some extent in sound output timing among the virtual occupants). Furthermore, "continuous call" means that the virtual occupants sequentially output the information corresponding to the content of the call by sounds after the call. Here, the "continuous call" includes the "repeated call" by the driver corresponding to preceding "call" by a virtual occupant, and further includes "continuous call" "repeated" by the "virtual occupants" at the same time. Note that, in the following embodiments, a case of mainly performing the "repeated call" will be described. However, similar processing is performed in the case of the "continuous call".

First Embodiment

FIG. 1 is a block diagram of a functional configuration of a drive assist device according to a first embodiment.

As illustrated in FIG. 1, a drive assist device 100 includes a navigation device 111, a vehicle control electronic control unit (ECU) 112, a gesture detection unit 113, a sound detection unit 114, a gaze detection unit 115, and a surrounding environment detection unit 116. In addition, the drive assist device 100 includes a drive assist ECU 120, a sound output unit 131, a display output unit 132, and a communication unit 133.

The drive assist device 100 is a device which is installed in a vehicle driven by a driver and assists cognitive activities of the driver at the time of driving by providing the driver with drive assist information using a sound output by the sound output unit 131 and a display output by the display output unit 132.

Figure 2A:
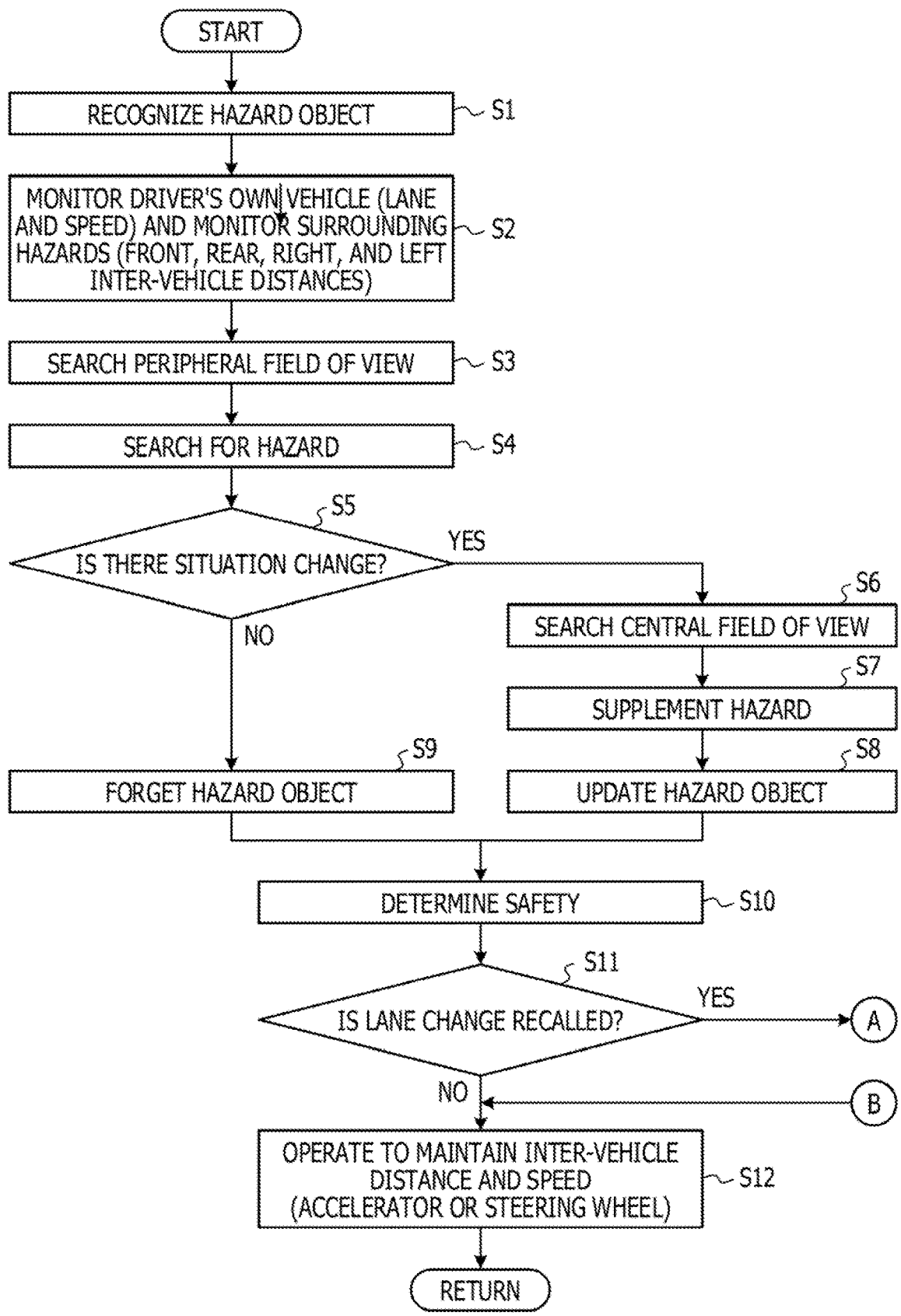

FIGS. 2A and 2B are an explanatory diagram for describing a cognitive structure model of a driver. The driver recognizes a surrounding situation as in a cognitive structure model illustrated in FIGS. 2A and 2B for example and performs a drive operation at the time of driving the vehicle.

Specifically, the driver recognizes hazardous places such as a pedestrian, and vehicles including a leading vehicle, a following vehicle, and an oncoming vehicle under the surrounding environment of the vehicle and the situation as hazard objects (S1). Then, the driver monitors the driver's own vehicle (such as a lane and a speed) and monitors surrounding hazard objects (such as distances between the vehicle and front, rear, right, and left vehicles) (S2).

In addition, the driver searches (S4) for the hazard object in searching (S3) a peripheral field of view in a view, and checks situation change of the hazard object (S5). In a case where there is the situation change (S5: YES), the driver searches for the hazard object in a central field of view (S6), and supplements the hazard object with the central field of view (S7) to update cognition of the hazard object (S8). In a case where there is no situation change (S5: NO), the driver does not supplement the hazard object in the central field of view, and forgetting of the hazard progresses (S9).

Next, the driver makes a safety determination on the basis of the recognized hazard object or the like (S10). For example, in a case where the driver does not recall lane change (S11: NO) according to presence or absence of recall of lane change (change from a driving lane to an overtaking lane) by safety determination (S11), the driver performs an operation (for an accelerator or a steering wheel) to maintain the inter-vehicle distance and speed (S12).

In a case where the driver has recalled the lane change (S11: YES), the driver performs risk prediction for the hazard object (S13), and performs safety check for risk avoidance (S14). Specifically, the driver performs safety check of a hazard ahead, safety check of a right rear hazard, and absence check of a hazard in a right blind spot according to a drive procedure.

Next, the driver makes a safety check decision and determines lane change (S15). The driver who has determined the lane change presents a blinker (S16), and rechecks the absence of the hazard in the right blind spot (S17), and then performs an operation for the lane change (for the accelerator or the steering wheel) (S18). Next, the driver performs safety check (S19) and completes the lane change (S20).

The drive assist device 100 detects the environment around the vehicle driven by the driver and generates a hazard list of an object to be a hazard on the basis of the detected environment, with respect to the cognitive structure model of the driver at the time of driving. Then, the drive assist device 100 detects a gaze of the driver and evaluates a risk (low interest) regarding driving of the driver for each object included in the hazard list on the basis of a frequency at which the object included in the hazard list is included in a field of view of the driver based on the detected gaze. Then, the drive assist device 100 outputs drive assist information corresponding to the object having the evaluated risk that is equal or larger than a threshold, using a sound output by the sound output unit 131 or a display output by the display output unit 132.

Therefore, the drive assist device 100 evaluates the risk for the object included in the hazard list detected by a peripheral monitoring sensor on the basis of the frequency of being included in the field of view of the driver, and provides the drive assist information corresponding to the object having the risk that is equal to or larger than the threshold, thereby suppressing excessive drive assist and realizing appropriate drive assist for the driver. For example, the drive assist device 100 does not provide the drive assist information for an object having a high frequency of being included in the field of view of the driver and recognized by the driver as an object of sufficiently high interest so as not to disturb the cognitive activities of the driver for the object. In addition, the drive assist device 100 provides the drive assist information for an object having a low frequency of being included in the field of view of the driver, and insufficiently recognized by the driver due to a decrease in interest, thereby suppressing the driver forgetting the object.

Returning to FIG. 1, the navigation device 111 detects a current position of the traveling vehicle using a global positioning system (GPS) and transmits the current position to the drive assist ECU 120 as position information. In addition, the navigation device 111 detects that the current position of the vehicle has reached a specific position such as an intersection, a branching point, or a meeting point, and includes a detection result (position detection result) in the position information and transmits the position information to the drive assist ECU 120.

Further, the navigation device 111 detects whether the driver's own vehicle travels straight, turning to the right, or turning to the left when the vehicle has reached the intersection on the basis of a route search result to a destination and a vehicle situation (such as a history of the drive operation and the speed of the vehicle). Similarly, the navigation device 111 detects whether the vehicle is branching to the left side or branching to the right side when the vehicle has reached the branching point on the basis of the route search result to the destination. Further, the navigation device 111 detects whether the vehicle is merging from the right side or merging from the left side when the vehicle has reached the meeting point on the basis of the route search result to the destination. The navigation device 111 includes these detection results (course detection results) in the position information and transmits the position information to the drive assist ECU 120.

The vehicle control ECU 112 acquires drive operation information (a steering angle of the steering wheel, an opening degree of an accelerator pedal, a depression amount of a brake pedal, and the like, for example) indicating the drive operation performed by the driver for the vehicle, vehicle information (a vehicle speed, for example) indicating a state of the vehicle, and the like. The vehicle control ECU 112 transmits the acquired drive operation information and vehicle information to the drive assist ECU 120.

The gesture detection unit 113 detects a gesture of the driver on the basis of an image of a vehicle interior captured by an on-vehicle camera (not illustrated) or the like. In addition, when detecting that the driver has performed a pointing action, the gesture detection unit 113 determines a pointing direction and transmits pointing direction information to the drive assist ECU 120.

The sound detection unit 114 detects call by the driver on the basis of a sound inside the vehicle collected by an on-vehicle microphone (not illustrated) or the like and transmits call information to the drive assist ECU 120.

The gaze detection unit 115 detects a gaze direction of the driver on the basis of a face image of the driver captured by the on-vehicle camera (not illustrated) or the like and transmits gaze direction information to the drive assist ECU 120.

The surrounding environment detection unit 116 detects obstacles such as pedestrians and other vehicles around the vehicle driven by the driver on the basis of detection information by the on-vehicle sensor (not illustrated), the on-vehicle camera (not illustrated), and the like, for example, and transmits surrounding environment information to the drive assist ECU 120. Specifically, the surrounding environment detection unit 116 transmits identification information for identifying the detected obstacles (the pedestrians, vehicles, and the like, for example), and the surrounding environment information including position information, speed information, and the like of the obstacles with respect to the vehicle driven by the driver to the drive assist ECU 120. That is, the surrounding environment detection unit 116 is an example of an environment detection unit. Note that, in the example in FIG. 1, the surrounding environment detection unit 116 directly transmits the detection result to the drive assist ECU 120 when detecting the obstacles such as the pedestrians and other vehicles. However, the surrounding environment detection unit 116 may input the detection result to the navigation device 111 or the vehicle control ECU 112. In this case, the navigation device 111 or the vehicle control ECU 112 analyzes the detection result and transmits the surrounding environment information to the drive assist ECU 120.

In addition, the surrounding environment detection unit 116 may acquire the surrounding environment information via road-to-vehicle communication or vehicle-to-vehicle communication and transmit the surrounding environment information to the drive assist ECU 120. In this case, the surrounding environment detection unit 116 functions as communication means.

The drive assist ECU 120 performs control for outputting the call attention message by sounds or by display. The drive assist ECU 120 stores a program for realizing various functions. The drive assist ECU 120 executes the program to function as a situation determination unit 121, an information specifying unit 122, an action determination unit 123, a hazard list generation unit 124, a risk evaluation unit 125, and an output control unit 126. In addition, the drive assist ECU 120 includes an action information storage unit 127 for storing various types of information such as action information, a hazard list, and a risk table, a hazard list storage unit 128, and a risk table storage unit 129.

Figure 3:
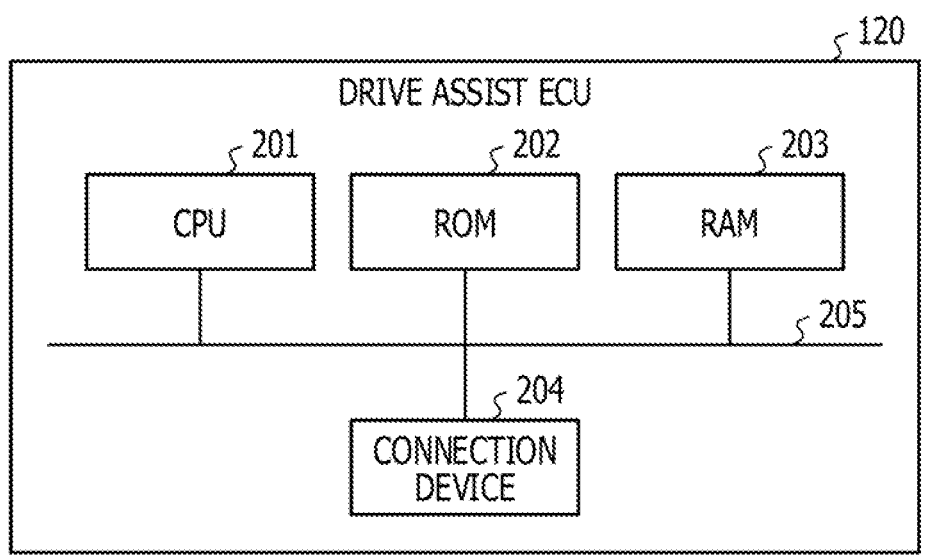
FIG. 3 is a block diagram illustrating an example of a hardware configuration of a drive assist ECU.

Here, a hardware configuration of the drive assist ECU 120 will be described. FIG. 3 is a block diagram illustrating an example of a hardware configuration of the drive assist ECU 120.

As illustrated in FIG. 3, the drive assist ECU 120 includes a central processing unit (CPU) 201, a read only memory (ROM) 202, a random access memory (RAM) 203, and a connection device 204. Note that the parts of the drive assist ECU 120 are connected to one another via a bus 205.

The CPU 201 is a computer that executes various programs stored in the ROM 202.

The ROM 202 is a non-volatile memory, and stores various programs executed by the CPU 201 and the information (the action information, the hazard list, the risk table, and the like) used when the various programs are executed.

The RAM 203 is a volatile memory, and provides a work area in which the various programs stored in the ROM 202 are expanded when executed by the CPU 201.

The connection device 204 connects the drive assist ECU 120 to an external device, and transmits and receives various types of information to and from the external device. Examples of the external device include the navigation device 111, the vehicle control ECU 112, the gesture detection unit 113, the sound detection unit 114, the gaze detection unit 115, the surrounding environment detection unit 116, the sound output unit 131, the display output unit 132, the communication unit 133, and the like.

Returning to FIG. 1, the situation determination unit 121 determines whether the current situation of the vehicle is in a situation in which the call attention message should be output to the driver in the vehicle on the basis of the position information received from the navigation device 111 and the action information stored in the risk evaluation unit 125. In the case of determining that the current situation is the situation in which the call attention message should be output to the driver in the vehicle, the situation determination unit 121 notifies the information specifying unit 122 of information regarding the current situation of the vehicle. Note that the situation determination unit 121 may further determine the current situation of the vehicle according to the surrounding environment information received from the surrounding environment detection unit 116.

When receiving the information regarding the current situation of the vehicle from the situation determination unit 121, the information specifying unit 122 specifies information used when the call attention message is output by sounds to the driver by reference to the action information in the action information storage unit 127, and notifies the output control unit 126 of the information. That is, the information specifying unit 122 is an example of a message specifying unit.

Specifically, the information specifying unit 122 acquires the call attention message and an ID of the message on the basis of the information regarding the current situation of the vehicle. In addition, the information specifying unit 122 specifies a direction that the driver should check on the basis of the acquired call attention message, and specifies a virtual outputting person defined in association with the specified direction. In addition, the information specifying unit 122 specifies timing and order to output sounds defined in association with the acquired call attention message. Further, the information specifying unit 122 notifies the output control unit 126 of these pieces of information as information used when the call attention message is output by sounds.

In addition, when acquiring the information regarding the current situation of the vehicle from the situation determination unit 121, the information specifying unit 122 specifies information used when appropriateness of a check action of the driver is determined by reference to the action information of the risk evaluation unit 125, and notifies the action determination unit 123 of the information.

Specifically, the information specifying unit 122 acquires the call attention message and an ID of the message on the basis of the information regarding the current situation of the vehicle. In addition, the information specifying unit 122 specifies order, pointing direction, call content, and gaze direction defined in association with the acquired call attention message. Then, the information specifying unit 122 notifies the action determination unit 123 of these pieces of information as the information used when the appropriateness of the check action of the driver is determined.

When acquiring the information used when the appropriateness of the check action of the driver is determined from the information specifying unit 122, the action determination unit 123 receives the pointing direction information from the gesture detection unit 113, receives the call information from the sound detection unit 114, and receives the gaze direction information from the gaze detection unit 115.

In addition, the action determination unit 123 determines whether at least any one of the received pointing direction information, call information, and gaze direction information corresponds to the information used when the appropriateness of the check action of the driver is determined, which has been acquired from the information specifying unit 122. In the case of determining that the at least any one of the information corresponds to the information, the action determination unit 123 determines that the driver of the vehicle has performed an appropriate check action.

In addition, the action determination unit 123 acquires, on the basis of a determination result as to whether the driver of the vehicle has performed the appropriate check action, a determination result message according to the determination result, and a virtual outputting person of the determination result message, from preset setting information and the like. Next, the action determination unit 123 notifies the output control unit 126 of the acquired determination result message and virtual outputting person.

The hazard list generation unit 124 generates the hazard list of the object to be a hazard around the vehicle on the basis of the surrounding environment information detected by the surrounding environment detection unit 116. Specifically, the hazard list generation unit 124 recognizes an obstacle detected by the surrounding environment detection unit 116 as the object to be a hazard and provides an object ID for identifying the object, and then stores the hazard list listing information (identification information, position information, speed information, and the like) for each object included in the surrounding environment information in the hazard list storage unit 128.

The risk evaluation unit 125 refers to the hazard list in the hazard list storage unit 128, and evaluates a risk regarding driving of the driver for each object included in the hazard list on the basis of the gaze direction information detected by the gaze detection unit 115. Next, the risk evaluation unit 125 outputs an evaluation result of the risk for each object included in the hazard list to the output control unit 126.

Specifically, the risk evaluation unit 125 obtains, for each object included in the hazard list, a frequency of being included in the field of view of the driver indicated by the gaze direction information. Then, the risk evaluation unit 125 calculates an oblivion degree indicating the degree of forgetfulness of the driver about the object according to the obtained frequency. For example, the risk evaluation unit 125 calculates the oblivion degree to be higher for the object having a lower frequency of being included in the field of view of the driver.

In addition, the risk evaluation unit 125 obtains hazard information objectively indicating the degree of hazard of the object with respect to the vehicle according to the position information and the speed information for each object included in the hazard list. The hazard information includes, for example, time-to-collision (TTC) that is a collision time to the vehicle for each object and the like. TTC is calculated by dividing the distance between the vehicle and the object by a speed difference (relative speed) on the basis of the position information and the speed information for each object.

Next, the risk evaluation unit 125 multiplies the oblivion degree for each object included in the hazard list by the hazard information such as TTC to obtain an evaluation value of the risk regarding driving of the driver for each object (hereinafter the evaluation value is referred to as a risk value). For example, an object having a higher oblivion degree and a higher risk has a higher risk value. Next, the risk evaluation unit 125 outputs the risk value for each object included in the hazard list to the output control unit 126.

The output control unit 126 acquires the call attention message, the ID of the message, the virtual outputting person, the timing, and the order notified from the information specifying unit 122. The output control unit 126 outputs the acquired call attention message by sounds via the sound output unit 131 at the acquired timing.

In addition, the output control unit 126 outputs the call attention message regarding the object having the risk value that is equal to or larger than a preset threshold by sounds via the sound output unit 131 on the basis of the risk value for each object included in the hazard list notified from the risk evaluation unit 125.

Specifically, the output control unit 126 acquires the position information of the object having the risk value that is equal to or larger than the present threshold by reference to the hazard list storage unit 128, and specifies the call attention message in which the direction to be checked in the call attention message and the position of the object match on the basis of the acquired position information.

Next, the output control unit 126 outputs the specified call attention message as the call attention message regarding the object by sounds via the sound output unit 131. Thereby, the drive assist device 100 can provide the driver with the call attention message about the object having a low frequency of being included in the field of view of the driver and insufficiently recognized by the driver, for example.

The action information storage unit 127 is, for example, a data table or the like, and stores the action information for each identification information such as an ID. FIGS. 4A and 4B are an explanatory diagram for describing an example of the action information storage unit 127.

As illustrated in FIGS. 4A and 4B, the action information storage unit 127 includes, as items of the action information, "position", "situation", "ID", "call attention message", "direction to be checked", "virtual outputting person", "timing", "order", "pointing direction", "call content", and "gaze direction".

In the "position", a position at which the call attention message should be output to the driver by sounds is defined. The example in FIGS. 4A and 4B illustrates that the call attention message is output by sounds in a case where the vehicle has reached any position of an intersection, a branching point, and a meeting point.

In the "situation", a situation of when the vehicle has reached any position of the intersection, the branching point, and the meeting point is defined. This is because the direction that the driver should check is different depending on the situation. For example, in a case where the situation of when the vehicle has reached the intersection is "straight ahead", the drive assist device 100 causes the driver to check left side and right side. In a case where the situation of when the vehicle has reached the intersection is "right turn", the drive assist device 100 causes the driver to check right front and ahead of right turn. Further, in a case where the situation of when the vehicle has reached the intersection is "left turn", the drive assist device 100 causes the driver to check ahead of left turn and left rear.

In the "ID", an identifier for identifying each "call attention message" output by sounds according to the "position" and the "situation" is stored.

In the "call attention message", a message to be output by sounds according to the "position" and the "situation" is stored. For example, in a case of the position="intersection" and the situation="straight ahead", "caution, intersection. stop and check", "check left", and "check right" are stored as messages to be output by sounds.

In the "direction to be checked", a direction that the driver should check by outputting the "call attention message" by sounds is defined. For example, in a case of the call attention message="intersection. please stop", the direction that the driver should check is front. Therefore, in the "direction to be checked", "front" is defined. In a case of the call attention message="check left side", the direction that the driver should check is a left direction. Therefore, in the "direction to be checked", "left side" is defined. Further, in a case of the call attention message="check right side", the direction that the driver should check is a right direction. Therefore, in the "direction to be checked", "right side" is defined.

In the "virtual outputting person", a virtual outputting person arranged at a position corresponding to the direction that the driver should check is defined by outputting the call attention message by sounds. For example, in a case of the direction to be checked="front", a virtual outputting person arranged at a position outside and in front of the vehicle is defined in the "virtual outputting person". Further, in a case of the direction to be checked="left side", a virtual occupant arranged at a position of a passenger's seat is defined in the "virtual outputting person". Furthermore, in a case of the direction to be checked="right side", a virtual outputting person arranged at the position outside and on the right side of the vehicle is defined in the "virtual outputting person".

In the "timing", timing to output the call attention message by sounds is defined. In the "order", an order to output the call attention message by sounds is defined.

Note that "L" represents a distance from the current position of the vehicle to the "position" (for example, the intersection) and "V" represents the current vehicle speed of the vehicle, in the expressions stored in the "timing".

For example, in the case of the position="intersection" and the situation="straight ahead", the call attention message of "caution, intersection. stop and check" is output by sounds (L/V+10) seconds before the vehicle reaches the intersection. Further, the call attention message of "check right" is output by sounds (L/V+5) seconds before the vehicle reaches the intersection. Furthermore, the call attention message of "check left" is output by sounds (L/V) seconds before the vehicle reaches the intersection. That is, in the case of the action information of the action information storage unit 127, the timing of sound output of the call attention message is determined on the basis of the current vehicle speed of the vehicle, and respective call attention messages are output by sounds in a defined order at predetermined intervals, in this case, at intervals of 5 seconds. A speech pause time of punctuation may be expanded or reduced depending on the situation.

In the "pointing direction", a direction of a pointing action that the driver should perform in response to the sound output of the call attention message is stored. In the "call content", a call content that the driver should perform in response to the sound output of the call attention message is stored. In the "gaze direction", a direction of a gaze that the driver should give in response to the sound output of the call attention message is stored.

Returning to FIG. 1, the hazard list storage unit 128 is a data table or the like, for example, and stores the hazard list generated by the hazard list generation unit 124. The risk table storage unit 129 is a data table or the like, for example, and stores information (for example, a check frequency, the oblivion degree, the risk value, flag information, and the like) regarding risk evaluation for each object included in the hazard list.

Figure 5:
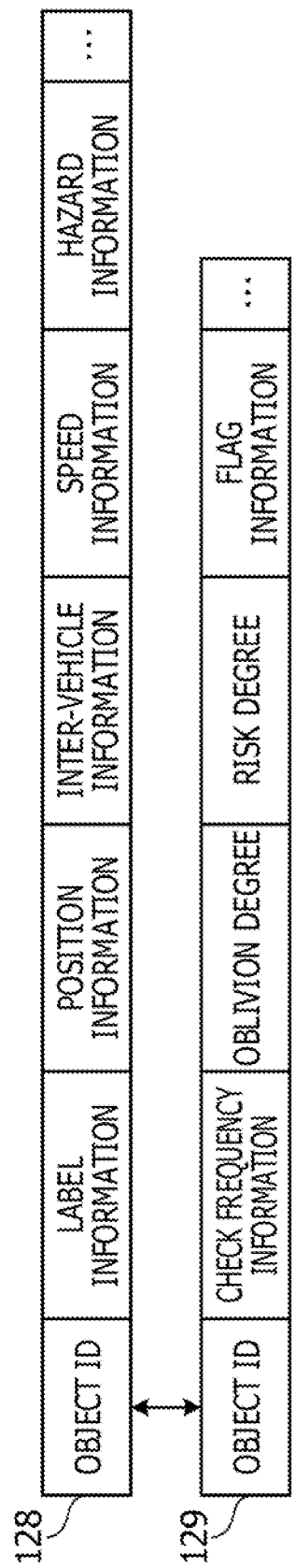
FIG. 5 is an explanatory diagram for describing examples of a hazard list storage unit and a risk table storage unit.

FIG. 5 is an explanatory diagram for describing examples of the hazard list storage unit 128 and the risk table storage unit 129. As illustrated in FIG. 5, information regarding the same object is associated with the object ID in the hazard list storage unit 128 and the risk table storage unit 129.

The hazard list storage unit 128 stores label information, position information, inter-vehicle information, speed information, and hazard information of the object for each object ID.

The label information is information labeled on the basis of identification content of the object (for example, a pedestrian, a vehicle, or the like), a positional relationship (front and back), and a relative speed. For example, label information such as "leading vehicle" is given to a vehicle traveling in front in the same direction, and "following vehicle" is given to a vehicle traveling behind in the same direction.

The position information, the inter-vehicle information, and the speed information indicate the position, inter-vehicle distance, a relative speed, and the like with respect to the vehicle of the driver based on the position information and the speed information of the object detected by the surrounding environment detection unit 116. The hazard information is, for example, TTC regarding the object calculated on the basis of the position information, inter-vehicle distance, and relative speed.

The risk table storage unit 129 stores, for each object ID, check frequency information, the oblivion degree, the risk value, and the flag information of the object. The check frequency information is information indicating the frequency at which the object is captured in the field of view of the driver, and is, for example, time when the presence of the object in the field of view is checked or the like.

The oblivion degree is a value indicating the degree of forgetfulness of the driver about the object, which is calculated by the risk evaluation unit 125. Similarly, the risk value is an evaluation value of the risk regarding driving of the driver for the object, which is calculated by the risk evaluation unit 125. The flag information is a flag assigned to the object. An example of the flag information includes a risk prediction flag indicating that the driver has predicted (recognized) a risk to the object by performing a drive operation (accelerator reduction or the like) for the object and the like, for example.

Returning to FIG. 1, the sound output unit 131 is a sound output device such as a speaker that outputs information by sounds under the control of the output control unit 126. The sound output unit 131 outputs by sounds the sound information (the call attention message, the determination result message, and the like) transmitted from the output control unit 126.

The display output unit 132 is a display, an indicator light, or the like that outputs information by display under the control of the output control unit 126. For example, as the display output unit 132, a liquid crystal display (LCD) provided on a dashboard or the like, a projection device for projecting information on a front windshield or the like can be applied. Further, the display output unit 132 may include an indicator light 132a (light emitting diode (LED), see FIG. 16) provided at a side mirror outside the vehicle or the like for outputting information by display outside the vehicle. In the present embodiment, the sound output has been mainly described. However, it goes without saying that the output of the call attention message and the determination result message may be the display output by the display output unit 132.

The communication unit 133 is a communication device that communicates with an external device by wireless communication under the control of the drive assist ECU 120. Specifically, the communication unit 133 performs road-to-vehicle communication, vehicle-to-vehicle communication, communication with a server device 501 (see FIG. 17) via a wireless local area network (LAN), or the like.

Figure 6:
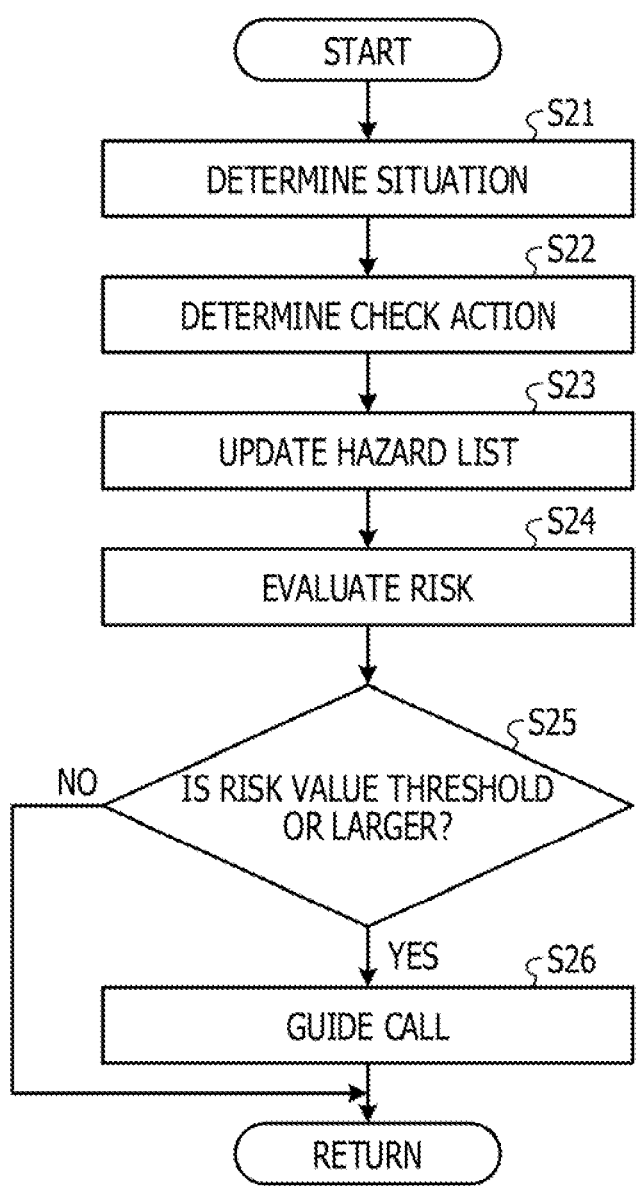
FIG. 6 is a flowchart illustrating an example of drive assist processing.

Next, a flow of drive assist processing executed by the drive assist ECU 120 will be described. FIG. 6 is a flowchart illustrating an example of the drive assist processing.

The drive assist processing illustrated in FIG. 6 is started when, for example, an ignition switch of the vehicle is turned on and the drive assist ECU 120 is activated. As illustrated in FIG. 6, when the processing is started, the situation determination unit 121 executes situation determination processing (S21).

Figure 7:
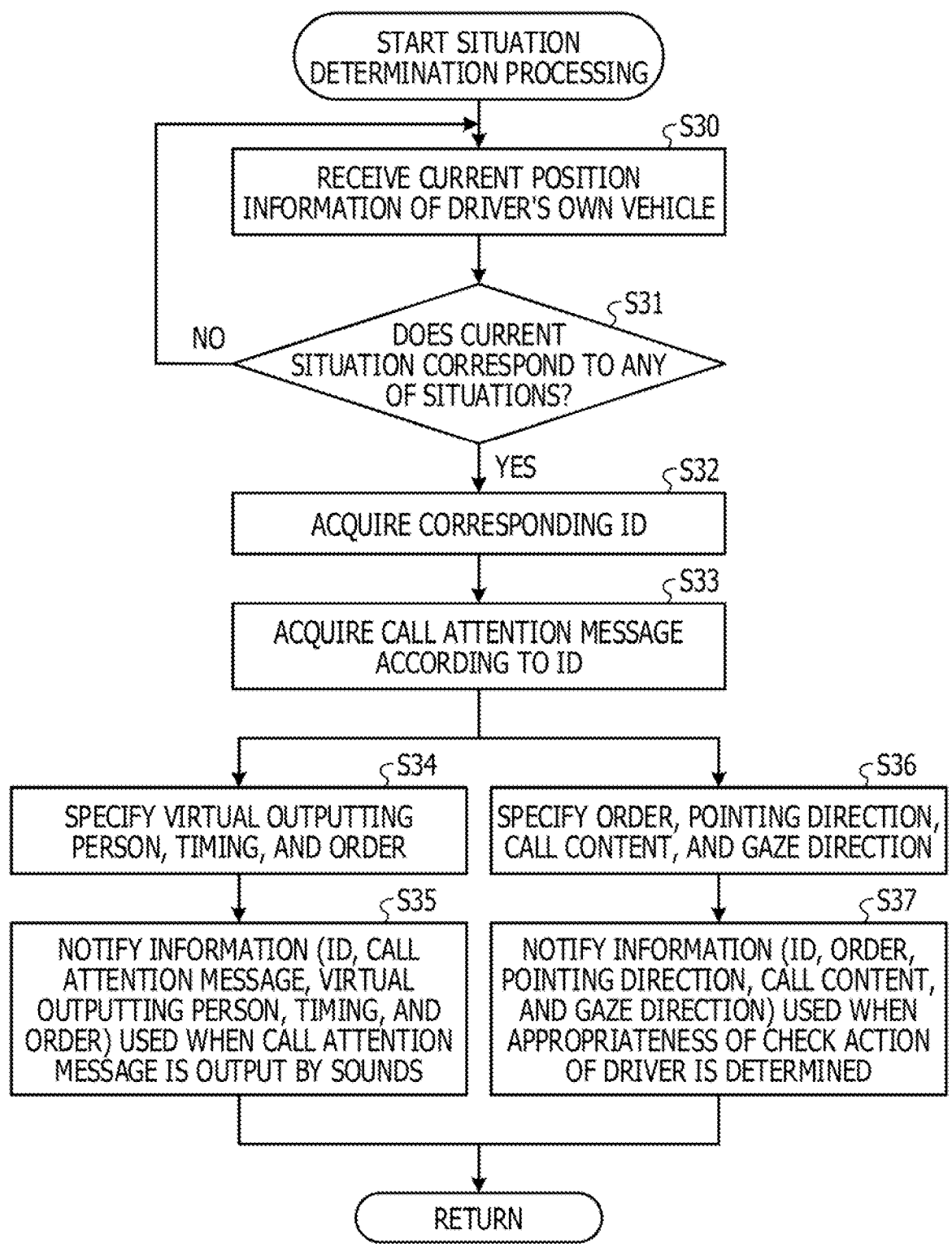
FIG. 7 is a flowchart illustrating an example of situation determination processing.

Here, details of the situation determination processing will be described. FIG. 7 is a flowchart illustrating an example of the situation determination processing. As illustrated in FIG. 7, when the situation determination processing is started, the situation determination unit 121 receives the current position information of the vehicle from the navigation device 111 (S30).

Next, the situation determination unit 121 extracts the position detection result and the course detection result included in the received position information. Note that the position detection result includes any of the intersection, the branching point, and the meeting point, and the course detection result includes any of straight ahead, right turn, left turn, branching to the right side, branching to the left side, merging from the right side, and merging from the left side.

Next, the situation determination unit 121 determines whether the current situation of the vehicle corresponds to the situation defined in the action information of the action information storage unit 127 on the basis of the position detection result and the course detection result (S31).

In the case where the current situation is determined not to correspond to the situation defined in the action information (S31: NO), the situation determination unit 121 returns the processing to S30. On the other hand, in the case where the current situation is determined to correspond to the situation defined in the action information (S31: YES), the information specifying unit 122 acquires the ID corresponding to the situation determined by the situation determination unit 121 from the action information of the action information storage unit 127 (S32).

For example, in the case where the vehicle is determined to be in the situation of traveling straight through the intersection, the information specifying unit 122 acquires ID="1", "2", and "3" from the action information (see FIGS. 4A and 4B).

Next, the information specifying unit 122 acquires the call attention message corresponding to the acquired ID (S33). For example, in the case where the acquired IDs are "1", "2", and "3", the information specifying unit 122 acquires "caution, intersection. stop and check", "check left", and "check right", as the corresponding call attention message (see FIGS. 4A and 4B).

Next, the information specifying unit 122 specifies the direction that the driver should check on the basis of the acquired call attention message by reference to the action information of the action information storage unit 127, and specifies the virtual outputting person defined in association with the specified direction. In addition, the information specifying unit 122 specifies the timing and order defined in association with the acquired call attention message by reference to the action information (S34).

Referring to the example in FIGS. 4A and 4B, in the case where the acquired call attention message is "caution, intersection. stop and check", for example, the information specifying unit 122 specifies "front" as the direction that the driver should check, and specifies the virtual outputting person="virtual outputting person outside and in front of vehicle" defined in association with the "front". Further, the information specifying unit 122 specifies the timing="before (L/V+10)" and the order="1" defined in association with the call attention message="caution, intersection. stop and check". Similarly, in the case where the acquired call attention message is "check left", the information specifying unit 122 specifies the virtual outputting person="virtual occupant on passenger's seat", the timing="before (L/V+5) seconds", and the order="2". Furthermore, in the case where the acquired call attention message is "check right", the information specifying unit 122 specifies the virtual outputting person="virtual passenger on the right outside vehicle", the timing="before (L/V) seconds", and the order="3".

Next, the information specifying unit 122 notifies the output control unit 126 of the acquired ID and call attention message, and the specified virtual outputting person, timing, and order, as the information used when the call attention message is output by sounds (S35).

Further, the information specifying unit 122 specifies the order, and the pointing direction, the call content, and the gaze direction of the driver defined in association with the acquired call attention message by reference to the action information (S36) in parallel to the processing in S34 and S35.

Referring to the example in FIGS. 4A and 4B, in the case where the acquired call attention message is "caution, intersection. stop and check", the information specifying unit 122 specifies the order "1", the pointing direction="front", the call content="stop clear", and the gaze direction="front". Further, in the case where the acquired call attention message is "check left", the information specifying unit 122 specifies the order "2", the pointing direction="left side", the call content="left clear", and the gaze direction="left side". Further, in the case where the acquired call attention message is "check right", the information specifying unit 122 specifies the order "3", the pointing direction="right side", the call content="right clear", and the gaze direction="right side".

Next, the information specifying unit 122 notifies the action determination unit 123 of the acquired ID, and the specified order, pointing direction, call content, and gaze direction, as the information used when the appropriateness of the check action of the driver is determined (S37). Thereafter, the information specifying unit 122 returns the processing.

Returning to FIG. 6, following S21, the information specifying unit 122 executes check action determination processing (S22).

Figure 8:
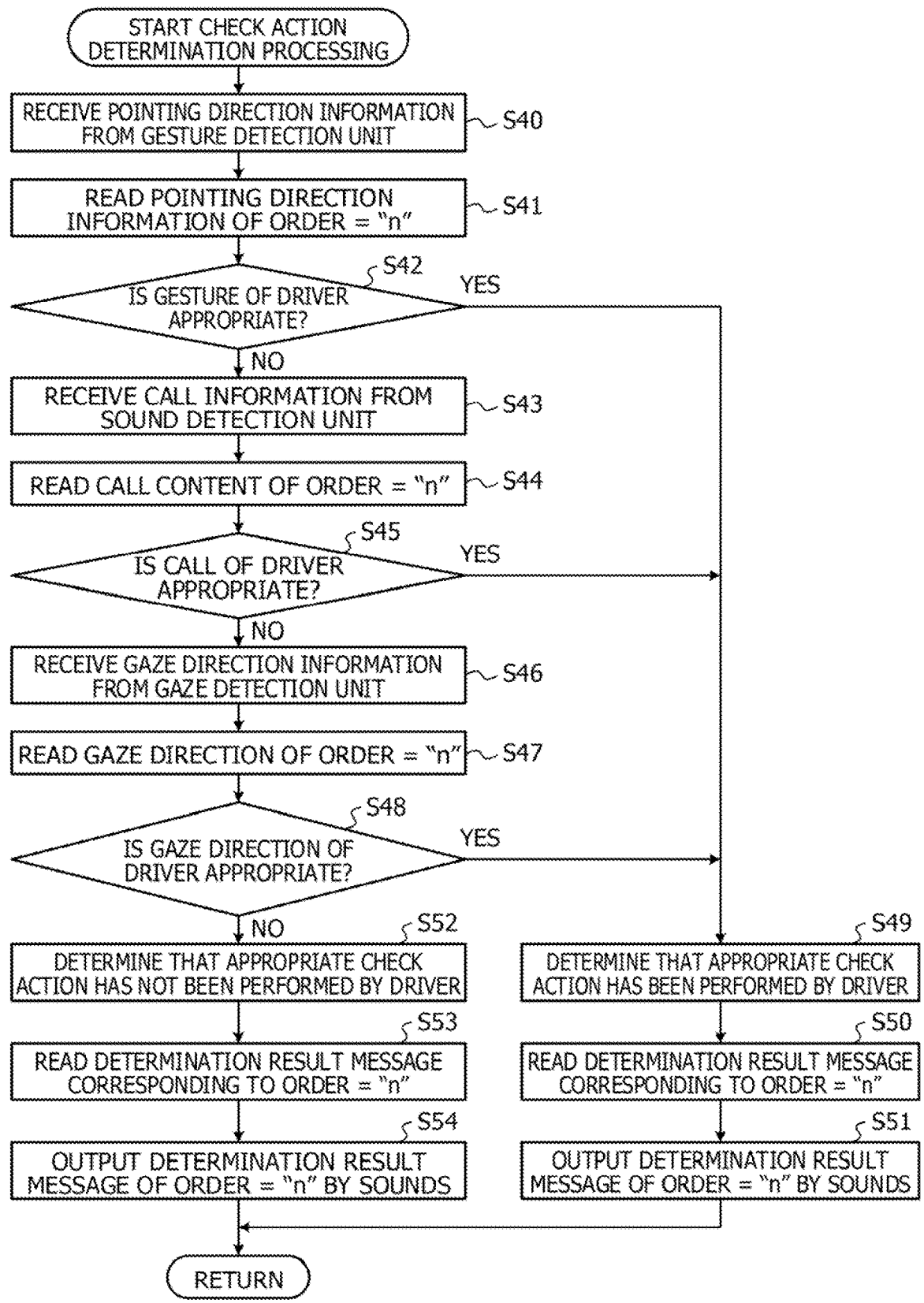
FIG. 8 is a flowchart illustrating an example of check action determination processing.

Here, details of the check action determination processing will be described. FIG. 8 is a flowchart illustrating an example of the check action determination processing. As illustrated in FIG. 8, when the check action determination processing is started, the action determination unit 123 receives the pointing direction information from the gesture detection unit 113 (S40).

Next, the action determination unit 123 reads the pointing direction corresponding to the order="n" out of pointing directions included in the information used when the appropriateness of the check action of the driver is determined, which has been notified from the information specifying unit 122 (S41). For example, in the case of the order="1", the action determination unit 123 reads the pointing direction="front".

Next, the action determination unit 123 determines whether the gesture of the driver is appropriate (S42). Specifically, the action determination unit 123 determines whether the pointing direction information acquired in S40 matches the "pointing direction" read in S41. In the case where the pointing direction information is determined to match the read pointing direction (S42: YES), the action determination unit 123 advances the processing to S49.

In the case where the pointing direction information is determined not to match the read pointing direction (S42: NO), the action determination unit 123 determines that the gesture (pointing action) of the driver is not appropriate and advances the processing to S43. In S43, the action determination unit 123 receives the call information from the sound detection unit 114.

Next, the action determination unit 123 reads the call content corresponding to the order="n" out of call contents included in the information used when the appropriateness of the check action of the driver is determined, which has been notified from the information specifying unit 122 (S44). For example, in the case of the order="1", the action determination unit 123 reads the call content="stop clear".

Next, the action determination unit 123 determines whether the call of the driver is appropriate (S45). Specifically, the action determination unit 123 determines whether the call information acquired in S43 matches the "call content" read in S44. In the case where the call information is determined to match the call content (S45: YES), the action determination unit 123 determines that the call of the driver is appropriate and advances the processing to S49.

In the case where the call information is determined not to match the call content (S45: NO), the action determination unit 123 determines that the call of the driver is not appropriate and advances the processing to S46. In S46, the action determination unit 123 receives the gaze direction information from the gaze detection unit 115.

Next, the action determination unit 123 reads the gaze direction corresponding to the order="n" out of gaze directions included in the information used when the appropriateness of the check action of the driver is determined, which has been notified from the information specifying unit 122 (S47). For example, in the case of the order="1", the action determination unit 123 reads the gaze direction="front".

Next, the action determination unit 123 determines whether the gaze direction of the driver is appropriate (S48). Specifically, the action determination unit 123 determines whether the gaze direction information received in S46 matches the "gaze direction" read in S47. In the case where the gaze direction information is determined to match the gaze direction (S48: YES), the action determination unit 123 determines that the gaze direction of the driver is appropriate and advances the processing to S49.

In the case where the gaze direction information is determined not to match the gaze direction (S48: NO), the action determination unit 123 determines that the gaze direction of the driver is not appropriate and advances the processing to S52.

In S49, the action determination unit 123 determines that the appropriate check action has been performed by the driver. Next, the action determination unit 123 reads determination result message and the virtual outputting person corresponding to the case where the appropriate check action has been performed from the preset setting information or the like and notifies the output control unit 126 of the read information (S50). Examples of the determination result message include sounds such as "good" praising for the appropriate check action and "check", a clear sound, and the like. Further, the virtual outputting person may be "all virtual occupants", or the like. Further, another "repeated call" by the virtual occupant ("continuous call") may be performed in time with the last call "good" so as not to disturb the continuous call by the driver.

Next, the output control unit 126 outputs by sounds the determination result message notified from the action determination unit 123 via the sound output unit 131 (S51). Thereby, the appropriate check action having been performed can be notified to the driver by the sounds such as "good" and "check", the clear sound, and the like. Thereafter, the output control unit 126 returns the processing.

In S52, the action determination unit 123 determines that the appropriate check action has not been performed by the driver. Next, the action determination unit 123 reads the determination result message and the virtual outputting person corresponding to the case where the appropriate check action has not been performed from the preset setting information or the like and notifies the output control unit 126 of the read information (S53). For example, examples of the determination result message include a sound such as "unchecked" indicating that the appropriate check action has not been performed, a beep sound, and the like. Further, the virtual outputting person may be "all virtual occupants", or the like.

Next, the output control unit 126 outputs by sounds the determination result message notified from the action determination unit 123 via the sound output unit 131 (S54). Thereby, the appropriate check action having not been performed can be notified to the driver by the sound such as "unchecked", the beep sound, and the like. Thereafter, the output control unit 126 returns the processing.

Returning to FIG. 6, following S22, the hazard list generation unit 124 updates (generates) the hazard list of the object to be a hazard around the vehicle on the basis of the surrounding environment information detected by the surrounding environment detection unit 116 (S23).

Figure 9:
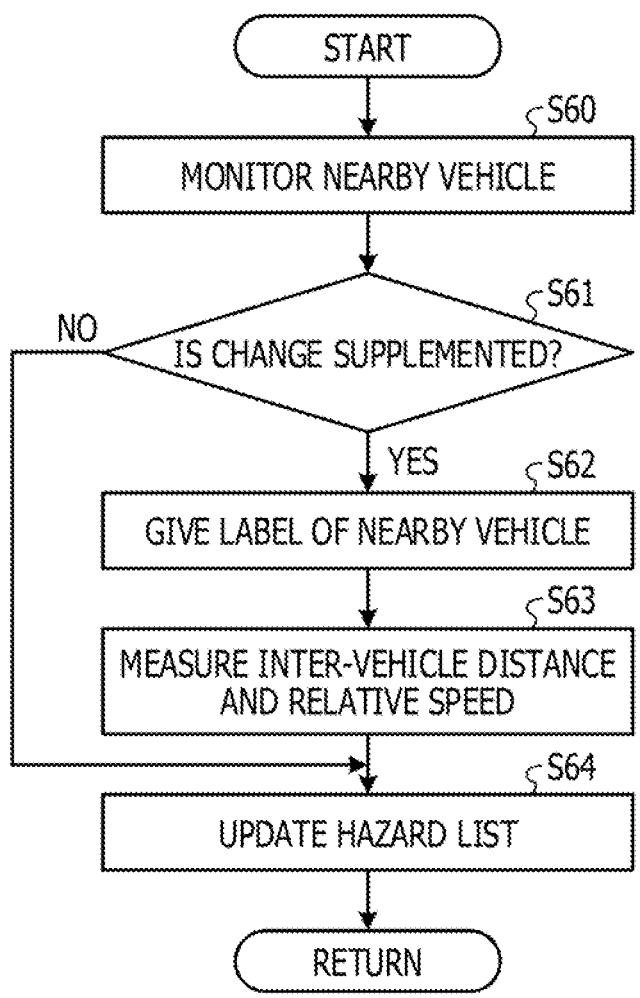
FIG. 9 is a flowchart illustrating an example of hazard list generation processing.

Here, details of hazard list update (generation) processing will be described. FIG. 9 is a flowchart illustrating an example of the hazard list generation processing.

As illustrated in FIG. 9, when the processing is started, the hazard list generation unit 124 monitors a vehicle around the vehicle driven by the driver on the basis of the surrounding environment information (S60). Next, as a result of the monitoring, the hazard list generation unit 124 determines whether change in the surrounding vehicle (for example, detection of a new vehicle, change in the position or speed of an already detected vehicle, or the like) has been supplemented (S61).

In the case where the change has been supplemented (S61: YES), the hazard list generation unit 124 gives a label such as "leading vehicle" or "following vehicle" on the basis of the surrounding environment information (S62) and measures the inter-vehicle distance and the relative speed (S63) for the vehicle (nearby vehicle) with supplemented change. Next, the hazard list generation unit 124 updates the hazard list in the hazard list storage unit 128 regarding the vehicle (object) with the supplemented change on the basis of the label given in S62, the inter-vehicle distance and the relative speed measured in S63, and the like (S64).

Note that, in the case where the change is not supplemented (S61: NO), the hazard list generation unit 124 skips S62 and S63 and advances the processing to S64. In this case, since there is no vehicle with supplemented change, the content of the hazard list in the hazard list storage unit 128 is not updated and kept unchanged. After S64, the hazard list generation unit 124 returns the processing.

Returning to FIG. 6, following S23, the risk evaluation unit 125 refers to the hazard list in the hazard list storage unit 128, and evaluates the risk regarding driving of the driver for each object included in the hazard list on the basis of the gaze direction information detected by the gaze detection unit 115 (S24).

Figure 10:
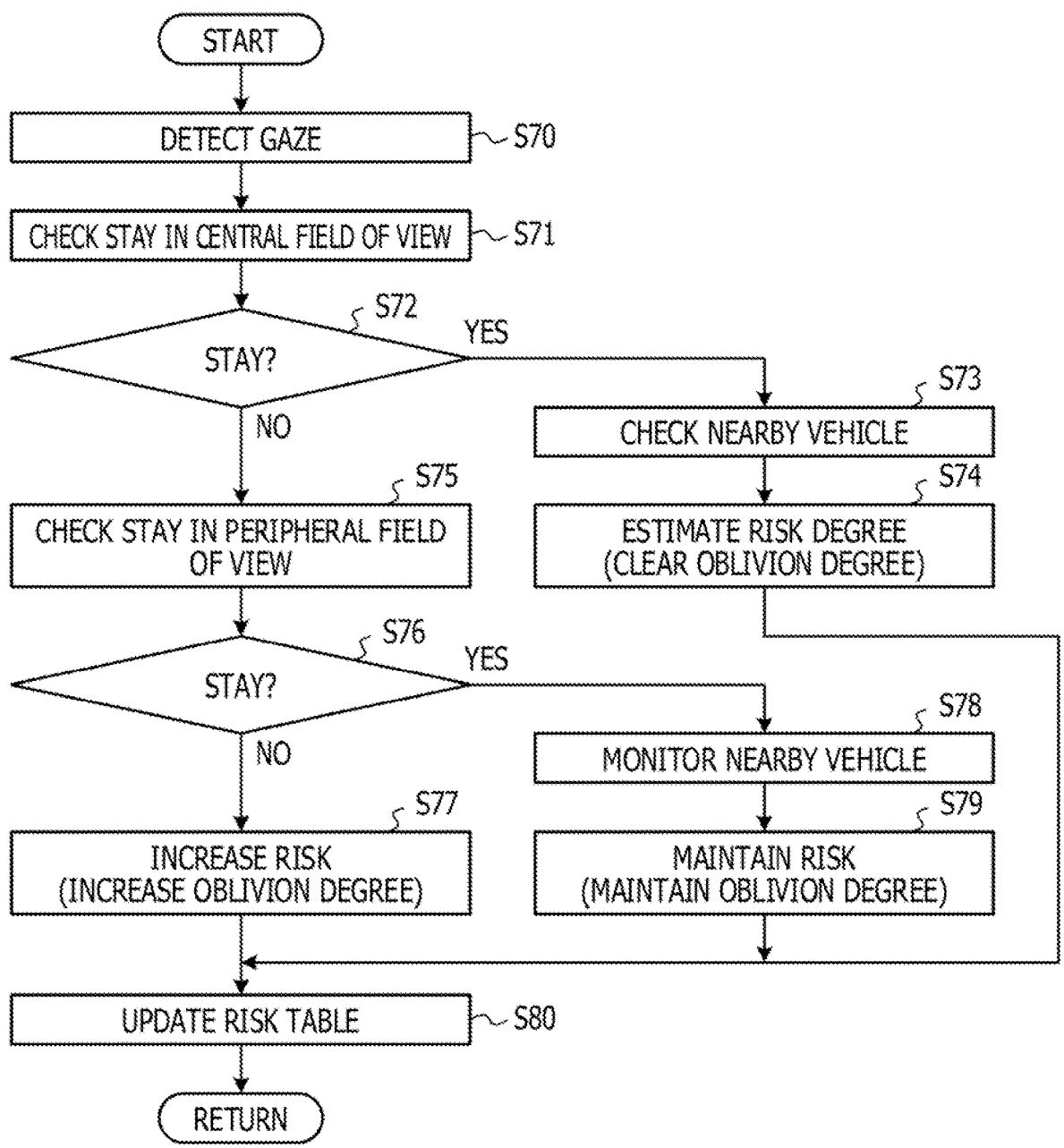
FIG. 10 is a flowchart illustrating an example of risk evaluation processing.

Here, details of the risk evaluation processing will be described. FIG. 10 is a flowchart illustrating an example of the risk evaluation processing.

As illustrated in FIG. 10, when the processing is started, the risk evaluation unit 125 detects the gaze of the driver on the basis of the gaze direction information from the gaze detection unit 115 and detects the direction of the field of view (the central field of view and the peripheral field of view) of the driver (S70). For example, in the case where the gaze of the driver is the front, the central field of view is "front" and the peripheral field of view is "right front", "left front", or the like.

Next, the risk evaluation unit 125 checks whether there is a stay in which the gaze stops for a predetermined period in the central field of view (S71) and determines the presence or absence of the stay (S72). In the case where there is a stay in the central field of view (S72: YES), the risk evaluation unit 125 checks the object (nearby vehicle) in the central field of view from the objects in the hazard list on the basis of the position information stored in the hazard list storage unit 128 (S73).

Next, the risk evaluation unit 125 evaluates the risk for the object checked to be in the central field of view. Specifically, the risk evaluation unit 125 obtains the hazard information such as TTC according to the position information and the speed information regarding the object included in the hazard list in the hazard list storage unit 128. Next, the risk evaluation unit 125 clears the oblivion degree (resets the value to a value indicating no oblivion) for the object most recently checked in the central field of view, and then multiplies the oblivion degree by the hazard information to estimate the risk value (S74).

In the case where there is no stay in the central field of view (S72: NO), the risk evaluation unit 125 checks whether there is a stay in which the gaze stops for a predetermined period in the peripheral field of view (S75) and determines the presence or absence of the stay (S76).

In the case where there is no stay in the peripheral field of view (S76: NO), the risk evaluation unit 125 evaluates the risk for the object outside the field of view. Specifically, the risk evaluation unit 125 obtains the hazard information such as TTC according to the position information and the speed information regarding the object included in the hazard list in the hazard list storage unit 128. Next, the risk evaluation unit 125 reads the previous risk value from the risk table storage unit 129, increases the oblivion degree from the previous value as the object outside the field of view, and then multiplies the oblivion degree by the hazard information to estimate the risk value (S77).

In the case where there is a stay in the peripheral field of view (S76: YES), the risk evaluation unit 125 checks the object (nearby vehicle) in the peripheral field of view from the objects in the hazard list on the basis of the position information stored in the hazard list storage unit 128 (S78).

Next, the risk evaluation unit 125 evaluates the risk for the object checked to be in the peripheral field of view. Specifically, the risk evaluation unit 125 obtains the hazard information such as TTC according to the position information and the speed information regarding the object included in the hazard list in the hazard list storage unit 128. Next, the risk evaluation unit 125 reads the previous risk value from the risk table storage unit 129, maintains the oblivion degree (the same value as previous time) as the object most recently checked in the peripheral field of view, and then multiplies the oblivion degree by the hazard information to estimate the risk value (S79).

FIG. 11 is an explanatory diagram illustrating risk calculation. As illustrated in FIG. 11, in S74, S77, and S79, the risk value is calculated by multiplying the oblivion degree corresponding to the check frequency by TTC calculated from the positional relationship, distance, relative speed, or the like, for each object included in the hazard list. Therefore, an object having a higher frequency of being included in the central field of view or the peripheral field of view of the driver is evaluated to have a lower risk among the objects included in the hazard list. Conversely, an object having a higher frequency of being located outside the field of view of the driver is evaluated to have a higher risk.

Following S74, S77, and S79, the risk evaluation unit 125 updates the risk table in the risk table storage unit 129 on the basis of the risk value estimated for the object (S80) and returns the processing.

Returning to FIG. 6, following S24, the output control unit 126 determines whether there is an object having a risk value that is equal or larger than a preset threshold on the basis of the risk value for each object included in the hazard list and notified from the risk evaluation unit 125 (S25).

In the case where there is the object having a risk value that is equal or larger than a preset threshold (S25: YES), the output control unit 126 outputs by sounds the call attention message regarding the determined object via the sound output unit 131 to guide the driver to the call (526). In the case where there is no object having a risk value that is equal or larger than a preset threshold (S25: NO), the output control unit 126 returns the processing.

Specifically, the output control unit 126 acquires the position information of the object having the risk value that is equal to or larger than the present threshold by reference to the hazard list storage unit 128, and specifies the call attention message in which the "direction to be checked" in the call attention message and the position of the object match on the basis of the acquired position information.

Figure 12B:
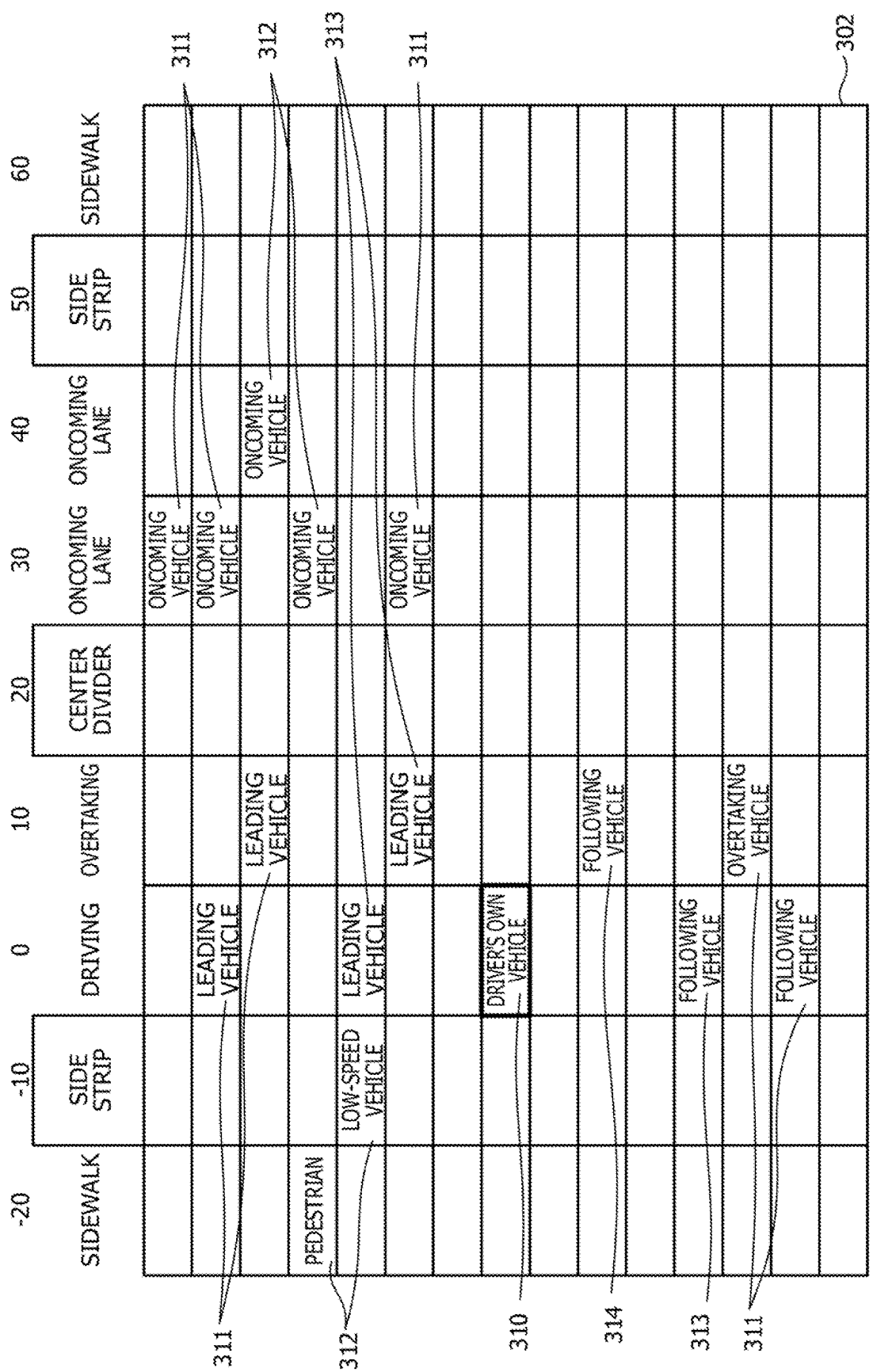

FIGS. 12A and 12B are an explanatory diagram for describing examples of a hazard map and a risk map. A hazard map 301 in FIGS. 12A and 12B illustrates the hazard list in the hazard list storage unit 128 in the form of a map. Similarly, a risk map 302 illustrates the content in the risk table storage unit 129 (objects 311 to 314 for a driver's own vehicle 310) in the form of a map. Here, risk values of the objects 311 to 314 are evaluated to 311<312<313<314, and the risk value of the object 314 is equal or larger than the threshold because of the high oblivion degree.

As described above, in the case where the position of the object 314 having the risk value that is equal or larger than the preset threshold is "right side", the output control unit 126 specifies a message with the "direction to be checked" being "right side" among the call attention messages notified from the information specifying unit 122.

As an example, assuming that messages with the ID of "1" to "3" among the call attention messages illustrated in FIGS. 4A and 4B are notified from the information specifying unit 122. In this case, since the position of the object is "right side", the output control unit 126 specifies a call attention message of "caution, right".

Next, the output control unit 126 outputs the specified call attention message as the call attention message regarding the object by sounds via the sound output unit 131. Thereby, the drive assist device 100 can provide the driver with the call attention message regarding the object having a low frequency of being included in the field of view of the driver and insufficiently recognized by the driver, for example. For example, the drive assist device 100 can provide the call attention message such as "caution, right" to guide the driver to the call for right side check. Of course, it goes without saying that emphasis of the meaning of words is possible by emphasizing punctuation.

FIG. 13 is an explanatory diagram for describing examples of check actions. In the case where the position of the object 314 having the risk value that is equal to or larger than the preset threshold is "right side", the call attention message such as "caution, right!" as in "#3" in FIG. 13 is provided to the driver. Thereby, the driver can re-recognize the object 314 whose oblivion degree becomes high and can be guided to check the call such as "right clear!" in "#4".

Further, the output control unit 126 outputs a determination result message such as a clear sound as in "#5", for the appropriate check action in "#4". Thereby, the drive assist device 100 can notify the driver that the appropriate check action is being performed.

Figure 14:
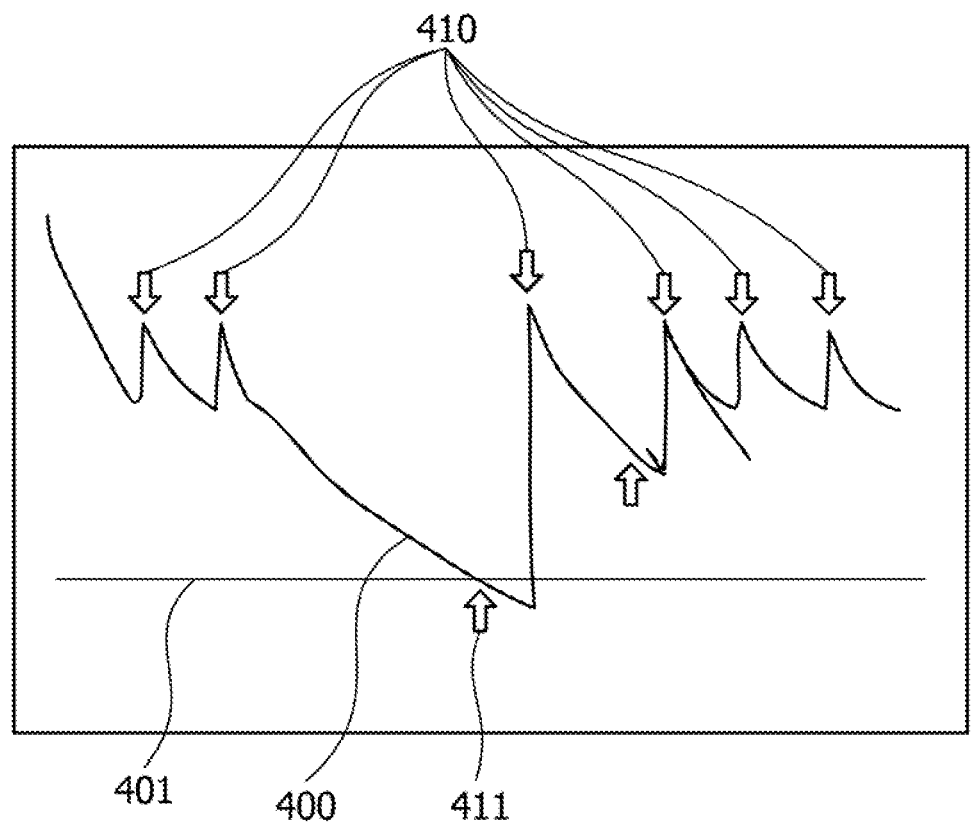
FIG. 14 is an explanatory diagram for describing an example of an oblivion degree of the driver with respect to an object.

FIG. 14 is an explanatory diagram for describing an example of an oblivion degree of the driver with respect to an object. FIG. 14 illustrates a graph 400 of the recognition degree of the object (a value that becomes larger as the degree of forgetfulness is lower in an opposite manner to the oblivion degree), and the vertical axis represents the value of the recognition degree and the horizontal axis represents time. As illustrated in FIG. 14, in a case where a cognitive activity 410 in which the driver captures the object in the field of view is frequent, the driver holds a certain recognition degree without forgetting the object. When the cognitive activity 410 has an interval and the graph 400 falls below a threshold 401 (the oblivion degree exceeds the threshold 401), the drive assist device 100 provides the driver of the call attention message with notification 411. As a result, the driver can re-recognize the object whose recognition degree becomes low.

Modification

The risk evaluation processing may be performed on the basis of not only the gaze of the driver but also whether the driver has predicted (recognized) the risk for the object by performing the drive operation (accelerator reduction or the like) for the object.

Figure 15:
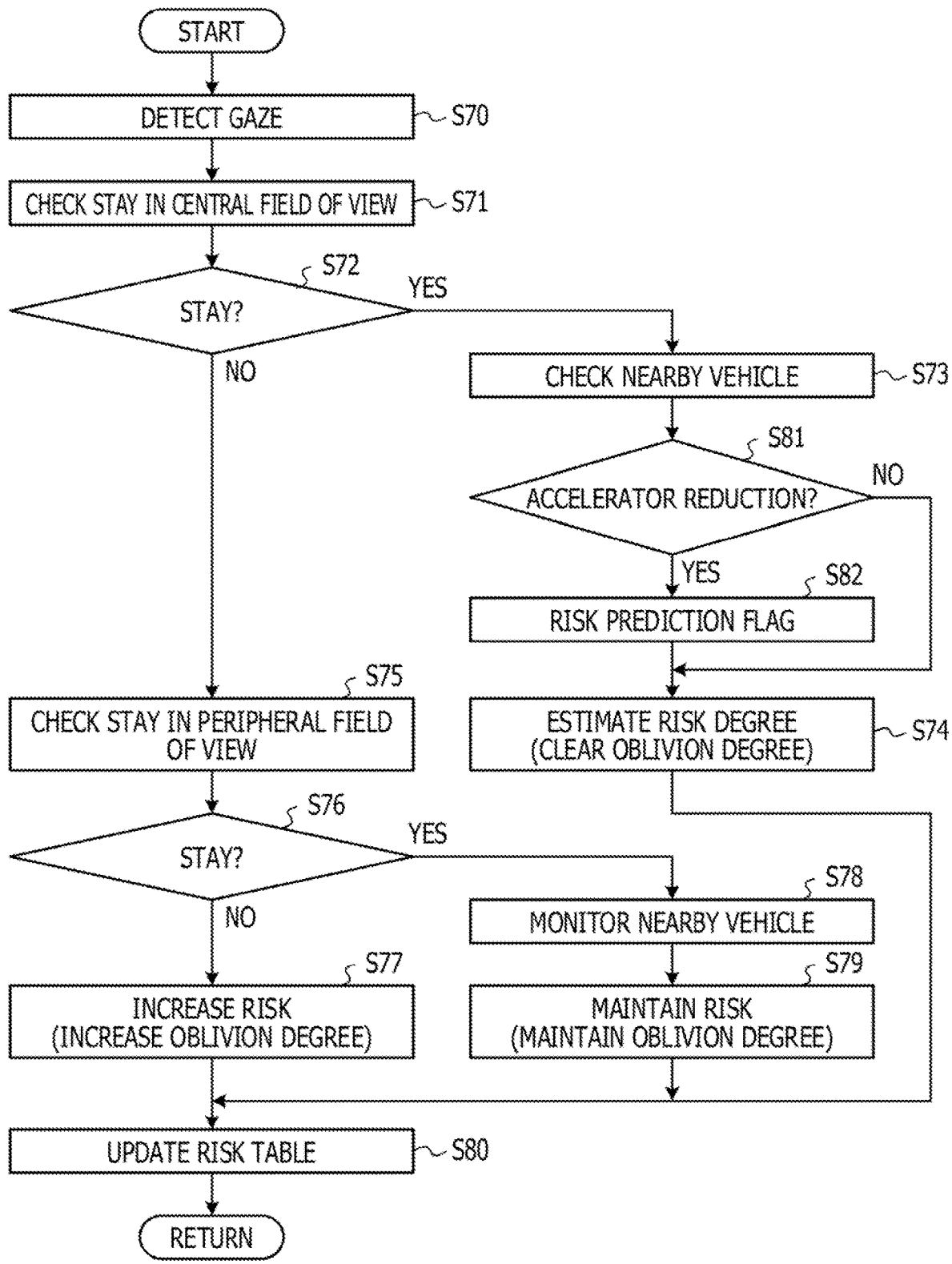
FIG. 15 is a flowchart illustrating a modification of the risk evaluation processing.

FIG. 15 is a flowchart illustrating a modification of the risk evaluation processing. As illustrated in FIG. 15, the risk evaluation unit 125 determines the presence or absence of the drive operation (accelerator reduction) for the nearby vehicle in the central field of view on the basis of the drive operation information from the vehicle control ECU 112 (S81). In the case where there is the drive operation (S81: YES), the risk prediction flag is stored in the flag information of the nearby vehicle in the risk table storage unit 129 (S82).

Next, the risk evaluation unit 125 calculates the risk value according to the presence or absence of the risk prediction flag in S74, S77, and S79. Specifically, in the case where there is the risk prediction flag, the risk evaluation unit 125 calculates the risk value to be lower than the case of no risk prediction flag because the driver predicts (recognizes) the risk for the object.

Further, the output control unit 126 may cause the display device provided outside the vehicle to display the presence or absence of the check action on the basis of the results in the check action determination processing (S40 to S54).

Figure 16:
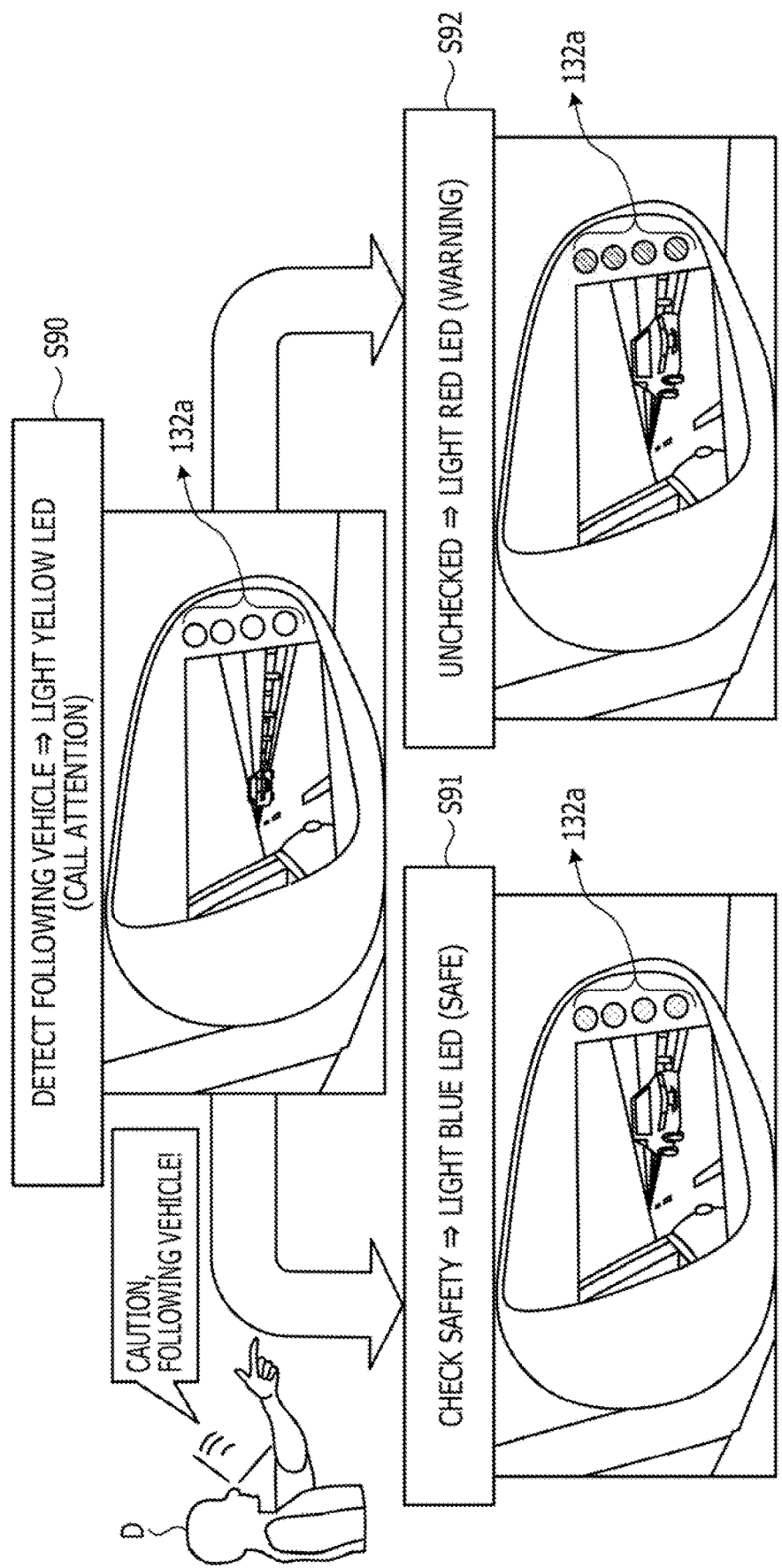
FIG. 16 is an explanatory diagram for describing a notification example to an outside of a vehicle.

FIG. 16 is an explanatory diagram for describing a notification example to the outside of the vehicle. As illustrated in FIG. 16, the output control unit 126 sets an indicator light 132a provided at a side mirror to lighting display (for example, yellow display) indicating calling attention, before check (S90). Next, in the case where the appropriate check action having been performed by a driver D is determined in the check action determination processing, the output control unit 126 sets the indicator light 132a to lighting display (for example, blue display) indicating safety check (S91).

Conversely, in the case where the appropriate check action having not been performed by the driver D is determined in the check action determination processing, the output control unit 126 sets the indicator light 132a to lighting display (for example, red display) indicating uncheck (S92). As described above, the indicator light 132a provided outside the vehicle outputs the display indicating the presence or absence of the check action by the driver D, whereby safety check can be performed between vehicles, for example.

In addition, the risk evaluation unit 125 may set a threshold for evaluating the risk value according to the drive mode (automatic drive mode, high-speed drive mode, leading vehicle following mode, manual drive mode, or the like) set by the driver D or the like. For example, immediately after the automatic drive mode is switched to the manual drive mode or the like, the cognitive activity may be a slow cognitive activity familiar to the automatic drive mode. Therefore, immediately after the automatic drive mode is switched to the manual drive mode or the like, the threshold may be set to be low to increase the frequency of outputting the call attention message. Further, since the cognitive activity as in the manual drive mode is not necessary in the automatic drive mode, the threshold may be set to be high to decrease the frequency of outputting the call attention message.

Second Embodiment

In the above-described first embodiment, a configuration of the drive assist device 100 alone has been illustrated. However, a server device having a similar function to the drive assist ECU 120 may be separately prepared from the drive assist device 100, and the drive assist device 100 and the server device connected to each other via a communication network may cooperate to realize the above-described functions.

Figure 17:
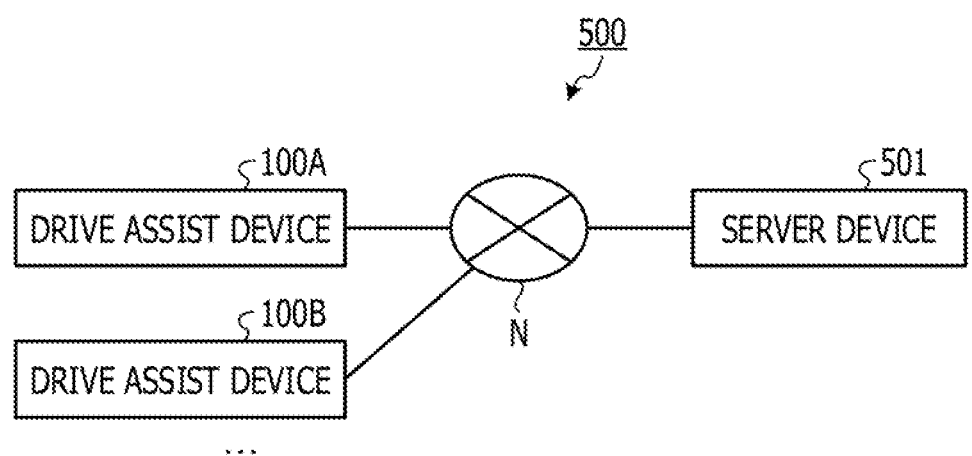
FIG. 17 is a block diagram of a functional configuration of a drive assist system according to a second embodiment.

FIG. 17 is a block diagram of a functional configuration of a drive assist system according to a second embodiment. As illustrated in FIG. 17, a drive assist system 500 has drive assist devices 100A and 100B and a server device 501 communicatively connected to one another via a communication network N such as a wireless LAN. The server device 501 provides the drive assist devices 100A, 100B, and the like connected via the communication network N with functions of a situation determination unit 121, an information specifying unit 122, an action determination unit 123, a hazard list generation unit 124, a risk evaluation unit 125, and the like in a drive assist ECU 120 described above. Further, the server device 501 includes a hazard list storage unit 128 and a risk table storage unit 129 for storing a hazard list and a risk table for each of the drive assist devices 100A, 100B, and the like, in addition to the action information storage unit 127.

With such a configuration of the drive assist system 500, the server device 501 has an advantage of mutually interpolating parts of respective pieces of information of the drive assist devices 100A, 100B, and the like. For example, in the hazard lists of vehicles close to each other, an object lacked in one hazard list may be interpolated from content of the other hazard list.

As described above, the drive assist device 100 includes a surrounding environment detection unit 116, the hazard list generation unit 124, a gaze detection unit 115, the risk evaluation unit 125, and an output control unit 126. The surrounding environment detection unit 116 detects an environment around a vehicle driven by a driver. The hazard list generation unit 124 generates a hazard list of an object to be a hazard on the basis of the detected environment. The gaze detection unit 115 detects a gaze of the driver. The risk evaluation unit 125 evaluates a risk regarding driving of the driver for each object included in the hazard list on the basis of a frequency at which the object included in the hazard list is included in a field of view of the driver based on the detected gaze. The output control unit 126 outputs drive assist information corresponding to the object having the evaluated risk that is equal to or larger than a threshold.

Thereby, the drive assist device 100 can suppress excessive drive assist and realize appropriate drive assist for the driver. For example, the drive assist device 100 does not provide the drive assist information for an object having a high frequency of being included in the field of view of the driver and sufficiently recognized by the driver so as not to disturb the cognitive activities of the driver for the object. In addition, the drive assist device 100 provides the drive assist information for an object having a low frequency of being included in the field of view of the driver, and insufficiently recognized by the driver, thereby suppressing the driver forgetting the object.

In addition, the risk evaluation unit 125 calculates an oblivion degree indicating the degree of forgetfulness of the driver about the object on the basis of whether the object included in the hazard list is included in the field of view of the driver based on the detected gaze. Then, the risk evaluation unit 125 evaluates a risk on the basis of the calculated oblivion degree and a collision time to the vehicle for each object included in the hazard list. The risk evaluation is performed on the basis of the oblivion degree of the driver about the object, that is, the recognition degree of the object, and the collision time when the object collides with the vehicle, that is, an objective risk of the object in this manner, whereby the risk evaluation of the object included in the hazard list can be appropriately performed.

Further, in a case where the object is included in a central field of view of the driver based on the gaze of the driver, the risk evaluation unit 125 resets a value of the oblivion degree of the object. Further, in a case where the object is included in a peripheral field of view of the driver based on the gaze of the driver, the risk evaluation unit 125 maintains the value of the oblivion degree of the object. Further, in a case where the object is not included in the central field of view and the peripheral field of view of the driver based on the gaze of the driver, the risk evaluation unit 125 increases the value of the oblivion degree of the object. By changing the evaluation of the oblivion degree of the driver for the object in the case where the object is not included in both the central field of view and the peripheral field of view of the driver in this manner, the risk evaluation of each object can be appropriately performed.

Note that the respective constituent elements of the illustrated apparatus and devices are not necessarily physically configured as illustrated in the drawings. That is, the specific aspects of separation and integration of each of the apparatus and devices are not limited to the illustrated aspects, and all or part of the apparatus or devices can be functionally or physically separated and integrated in any unit, in accordance with various loads, use status, and the like.

In addition, various processing functions performed by the drive assist device 100, 100A, 100B, or the server device 501 may be entirely or optionally partially executed on a central processing unit (CPU) (or a microcomputer, such as a microprocessor unit (MPU) or a micro controller unit (MCU)). In addition, it is needless to say that whole or any part of various processing functions may be executed by a program to be analyzed and executed on a CPU (or a microcomputer, such as an MPU or an MCU), or on hardware by wired logic. In addition, various processing functions performed by the server device 501 may be executed by a plurality of computers in cooperation though cloud computing.

The various processing functions described in the above embodiment can be realized by execution of a prepared program on a computer. This program may not be stored in a memory of the computer or the like. For example, the computer may read the program stored in a computer-readable storage medium and may execute the program. The computer-readable storage medium corresponds to, for example, a portable recording medium such as a CD-ROM, a DVD disk, and a universal serial bus (USB), a semiconductor memory such as a flash memory, a hard disk drive, and the like. Alternatively, the program may be prestored in a device connected to a public line, the Internet, a LAN, or the like, and the computer may read the program from the device and execute the program.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing device comprising:
a memory; and
a processor coupled to the memory and configured to:
detect an environment around a vehicle which is driven by a driver;
generate a hazard list of an object to be a hazard based on the detected environment;
detect a gaze of the driver;
acquire a frequency at which the object included in the hazard list is included in a field of view of the driver based on the detected gaze;
evaluate a risk indicating low interest to each object included in the hazard list regarding driving of the driver based on the frequency; and
output drive assist information corresponding to the object with the evaluated risk that is equal to or larger than a threshold.

2. The information processing device according to claim 1, wherein the processor is configured to:
calculate an oblivion degree indicating the degree of forgetfulness of the driver for the object based on whether the object included in the hazard list is included in the field of view of the driver based on the detected gaze; and
evaluates the risk based on the calculated oblivion degree and a collision time to the vehicle for the each object included in the hazard list.

3. The information processing device according to claim 2, wherein the processor is configured to:
reset a value of the oblivion degree of the object in a case where the object is included in a central field of view of the driver based on the gaze;
maintain the value of the oblivion degree of the object in a case where the object is included in a peripheral field of view of the driver based on the gaze; and
increase the value of the oblivion degree of the object in a case where the object is not included in the central field of view and the peripheral field of view of the driver based on the gaze.

4. The information processing device according to claim 1, wherein the processor is configured to:
determine a situation of the vehicle operated by the driver;
specify a message drawing driver's attention based on the determined situation; and
output a message corresponding to the object with the evaluated risk that is equal to or larger than the threshold among the specified messages as the drive assist information.

5. The information processing device according to claim 4, wherein the processor is configured to:
determine whether the driver is performed a check action corresponding to the determined situation; and
output a message corresponding to the check action in a case where the check action is determined to be performed.

6. The information processing device according to claim 5, wherein the processor is configured to cause a display device provided outside the vehicle to display presence or absence of the check action.

7. The information processing device according to claim 1, wherein the processor is configured to: set the threshold based on a drive mode of the vehicle.

8. A drive assist system comprising:
a server device; and
a drive assist device which is communicatively coupled via a communication network,
wherein the drive assist device is configured to:
detect an environment around a vehicle which is driven by a driver; and
detect a gaze of the driver,
wherein the server device is configured to:
generate a hazard list of an object to be a hazard based on the detected environment;
acquire a frequency at which the object included in the hazard list is included in a field of view of the driver based on the detected gaze;
evaluate a risk indicating low interest to each object included in the hazard list regarding driving of the driver based on the frequency; and output drive assist information corresponding to the object with the evaluated risk that is equal to or larger than a threshold.

9. The drive assist system according to claim 8, wherein the server device is configured to:
calculate an oblivion degree indicating the degree of forgetfulness of the driver for the object on the basis of whether the object included in the hazard list is included in the field of view of the driver based on the detected gaze; and
evaluate the risk based on the calculated oblivion degree and a collision time to the vehicle for the each object included in the hazard list.

10. The drive assist system according to claim 9, wherein the server device is configured to;
reset a value of the oblivion degree of the object in a case where the object is included in a central field of view of the driver based on the gaze;
maintain the value of the oblivion degree of the object in a case where the object is included in a peripheral field of view of the driver based on the gaze; and
increase the value of the oblivion degree of the object in a case where the object is not included in the central field of view and the peripheral field of view of the driver based on the gaze.

11. The drive assist system according to claim 8, the server device is configured to:
determine a situation of the vehicle operated by the driver;
specify a message drawing driver's attention based on the determined situation; and
output a message corresponding to the object with the evaluated risk that is equal to or larger than the threshold among the specified messages as the drive assist information.

12. The drive assist system according to claim 11, the server device is configured to:
determine whether the driver performs a check action corresponding to the determined situation; and
output a message corresponding to the check action in a case where the check action is determined to be performed.

13. The drive assist system according to claim 12, wherein the server device is configured to cause the drive assist device to cause a display device provided outside the vehicle to display presence or absence of the check action.

14. The drive assist system according to claim 8, wherein the server device is configured to set the threshold based on a drive mode of the vehicle.

15. A drive assist method comprising:
detecting, by a computer, an environment around a vehicle which is driven by a driver;
generating a hazard list of an object to be a hazard based on the detected environment;
detecting a gaze of the driver;
acquiring a frequency at which the object included in the hazard list is included in a field of view of the driver based on the detected gaze;
evaluating a risk indicating low interest to each object included in the hazard list regarding driving of the driver based on the frequency; and
outputting drive assist information corresponding to the object with the evaluated risk that is equal to or larger than a threshold.

16. The drive assist method according to claim 15, further comprising:
calculating an oblivion degree indicating the degree of forgetfulness of the driver for the object based on whether the object included in the hazard list is included in the field of view of the driver based on the detected gaze; and
evaluating the risk on the basis of the calculated oblivion degree and a collision time to the vehicle for the each object included in the hazard list.

17. The drive assist method according to claim 16, further comprising:
resetting a value of the oblivion degree of the object in a case where the object is included in a central field of view of the driver based on the gaze;
maintaining the value of the oblivion degree of the object in a case where the object is included in a peripheral field of view of the driver based on the gaze; and
increasing the value of the oblivion degree of the object in a case where the object is not included in the central field of view and the peripheral field of view of the driver based on the gaze.

18. The drive assist method according to claim 15, further comprising:
determining a situation of the vehicle operated by the driver; and
specifying a message drawing driver's attention on the basis of the determined situation, wherein the processing of outputting outputs a message corresponding to the object with the evaluated risk that is equal to or larger than the threshold among the specified messages as the drive assist information.

19. The drive assist method according to claim 18, further comprising:
determining whether the driver has performed a check action corresponding to the determined situation, wherein the processing of determining outputs a message corresponding to the check action in a case where the check action is determined to have been performed.

20. The drive assist method according to claim 15, wherein the processing of outputting sets the threshold based on a drive mode of the vehicle.

* * * * *